(12) United States Patent
Scher et al.

(10) Patent No.: US 9,096,905 B2
(45) Date of Patent: Aug. 4, 2015

(54) DETECTING DNA METHYLATION OF BCL2, CDKN2A AND NID2 GENES TO PREDICT BLADDER CANCER IN HUMANS

(71) Applicants: Michael Scher, Lawrenceville, NJ (US); Jason Trama, Burlington, NJ (US)

(72) Inventors: Michael Scher, Lawrenceville, NJ (US); Jason Trama, Burlington, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 40 days.

(21) Appl. No.: 13/773,834

(22) Filed: Feb. 22, 2013

(65) Prior Publication Data

US 2013/0224738 A1    Aug. 29, 2013

Related U.S. Application Data

(60) Provisional application No. 61/602,327, filed on Feb. 23, 2012.

(51) Int. Cl.
*C12Q 1/68*    (2006.01)

(52) U.S. Cl.
CPC ........ *C12Q 1/6886* (2013.01); *C12Q 2600/154* (2013.01); *C12Q 2600/158* (2013.01)

(58) Field of Classification Search
CPC ........... C12Q 1/6886; C12Q 2600/154; C12Q 2600/158
See application file for complete search history.

(56) References Cited

U.S. PATENT DOCUMENTS

| 2005/0239101 A1* | 10/2005 | Sukumar et al. | 435/6 |
| 2012/0039993 A1* | 2/2012 | Otto et al. | 424/450 |

FOREIGN PATENT DOCUMENTS

| JP | 2010161984 A | * | 7/2010 |
| WO | WO 2003044226 A3 | * | 3/2004 |
| WO | WO 2004087957 A2 | * | 10/2004 |
| WO | WO 2006004597 A2 | * | 1/2006 |
| WO | WO 2007116417 A1 | * | 10/2007 |

OTHER PUBLICATIONS

Fackler et al. (Quantitative Multiplex Methylation-Specific PCR Assay for the Detection of Promoter Hypermethylation in Multiple Genes in Breast Cancer, Cancer Research 64, 4442-4452, Jul. 1, 2004).*
Swift-Scanlon et al. (Two-color quantitative multiplex methylation-specific PCR, BioTechniques 40:210-219 (Feb. 2006)).*
Licchesi et al. (Methylation-Specific PCR, in DNA Methylation: Methods and Protocols, Second Edition, vol. 507, 2009).*
Derks et al. (Methylation-specific PCR unraveled, Cellular Oncology 26 (2004) 291-299).*
Lo et al. (MethySYBR, a Novel Quantitative PCR Assay for the Dual Analysis of DNA Methylation and CpG Methylation Density, Journal of Molecular Diagnostics, vol. 11, No. 5, Sep. 2009).*
Renard et al. (Identification and Validation of the Methylated TWIST1 and NID2 Genes through Real-Time Methylation-Specific Polymerase Chain Reaction Assays for the Noninvasive Detection of Primary Bladder Cancer in Urine Samples, European Urology 58 (2010) 96-104).*
Hogue et al. (Quantitation of Promoter Methylation of Multiple Genes in Urine DNA and Bladder Cancer Detection, Journal of the National Cancer Institute, vol. 98, No. 14, Jul. 19, 2006).*
Friedrich et al. (Detection of Methylated Apoptosis-Associated Genes in Urine Sediments of Bladder Cancer Patients, Clinical Cancer Research, vol. 10, 7457-7465, Nov. 15, 2004).*
Zimbardi et al. (Epigenetic Biomarkers in Bladder Cancer, in Bladder Cancer—From Basic Science to Robotic Surgery, Feb. 1, 2012).*
Kim et al. (Epigenetic Biomarkers in Urothelial Bladder Cancer, Expert Rev Mol Diagn. 2009;9(3):259-269).*
Yu et al. (A Novel Set of DNA MethylationMarkers in Urine Sediments for Sensitive/Specific Detection of Bladder Cancer, Clin Cancer Res 2007;13(24) Dec. 15, 2007).*
Shivapurkar et al. (Differential Methylation of a Short CpG-Rich Sequence within Exon 1 of TCF21 Gene: A Promising Cancer Biomarker Assay, Cancer Epidemiol Biomarkers Prev. Apr. 2008 ; 17(4): 995-1000).*
Fraga et al. (Real-Time PCR, in Current Protocols Essential Laboratory Techniques, 2008).*
Li et al. (MethPrimer: designing primers for methylation PCRs, Bioinformatics, Nov. 2002, 18(10): 1427-1431).*
Brandes et al. (Optimal primer design using the novel primer design program: MSPprimer provides accurate methylation analysis of the ATM promoter, Oncogene (2007) 26, 6229-6237).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
NCBI Accession Nos. NM_000633 (1979), NM_001101 (1978), NM_000077 (1995) and NM_007361 (1998).*
Brait, M., et al., Aberrant Promoter Methylation of Multiple Genes during Pathogenesis of Bladder Cancer, Cancer Epidemiology, Biomarkers & Prevention, Oct. 8, 2008, 17(10):2786-2794, American Association of Cancer Research.
Chung, W., et al., Detection of Bladder Cancer Using Novel DNA Methylation Biomarkers in Urine Sediments, Cancer Epidemiology, Biomarkers & Prevention, May 17, 2011, 20(7): 1483-1491, American Association of Cancer Research.
Costa, V., et al., Three epigenetic biomarkers, GDF15, TMEFF2 and VIM, accurately predict bladder cancer from DNA-based analyses of urine samples, Clinical Cancer Research, Oct. 25, 2010, 16(23):5842-5851, American Association of Cancer Research.

(Continued)

*Primary Examiner* — Stephanie K Mummert
*Assistant Examiner* — Aaron Priest
(74) *Attorney, Agent, or Firm* — Siu K. Lo

(57) ABSTRACT

The present invention provides a method of detecting DNA methylation of a plurality of genes consisting of CDKN2A, BCL2 and NID2 in a urine sample from a human. Methods and compositions are provided herein for detecting and diagnosing bladder cancer by obtaining a urine sample from a human subject suspected of bladder cancer, followed by detecting DNA methylation of CDKN2A, BCL2 AND NID2 in urine samples from the individual. The present method permits specific detection of DNA methylation of the selected gene promoters in urine as a biomarker for bladder cancer in humans.

9 Claims, 2 Drawing Sheets

(56) References Cited

OTHER PUBLICATIONS

Dulaimi, E., et al., Detection of Bladder Cancer in Urine by a Tumor Suppressor Gene Hypermethylation Panel, Clinical Cancer Research, Mar. 24, 2004, 10(6):1887-1893, American Association of Cancer Research.

Friedrich, M., et al., Detection of Methylated Apoptosis-Associated Genes in Urine Sediments of Bladder Cancer Patients, Clinical Cancer Research, Nov. 14, 2004,10(22): 7457-7465, American Association of Cancer Research.

Hoque, M., et al., Quantitation of Promoter Methylation of Multiple Genes in Urine DNA and Bladder Cancer Detection, Journal of the National Cancer Institute, Jul. 19, 2006, 98(14): 996-1004, Oxford University Press.

Hoque, M., et al., Genome-Wide Promoter Analysis Uncovers Portions of the Cancer Methylome, Cancer Research, Apr. 15, 2008, 68(8): 2661-2670, American Association of Cancer Research.

Reinert, T., et al., Comprehensive Genome Methylation Analysis in Bladder Cancer Identification and Validation of Novel Methylated Genes and Application of These as Urinary Tumor Markers, Clinical Cancer Research, Jul. 25, 2011, 17(17):5582-5592, American Association of Cancer Research.

Renard, I., et al., Identification and Validation of the Methylated TWIST1 and NID2 Genes through Real-Time Methylation-Specific Polymerase Chain Reaction Assays for the Noninvasive Detection of Primary Bladder Cancer in Urine Samples, European Urology, Sep. 1, 2009, 58(1):96-104, Elsevier.

Siegel, R., et al., Cancer Statistics, 2011: The Impact of Eliminating Socioeconomic and Racial Disparities on Premature Cancer Deaths, CA: A Cancer Journal for Clinicians, Jun. 17, 2011, 61(4):212-236, American Cancer Society.

Valenzuela, M.T., et al., Assessing the use of p16(INK4a) /Promoter Gene Methylation in Serum for Detection of Bladder Cancer, European Urology, Nov. 2002, 42(6): 622-628, Elsevier.

Vinci, S., et al, Quantitative methylation analysis of BCL2, hTERT, and DAPK promoters in urine sediment for the detection of non-muscle-invasive urothelial carcinoma of the bladder: A prospective, two-center validation study, Urologic Oncology, Jan. 12, 2009, 29(2): 150-156, Elsevier.

Melnikov., et al., MSRE-PCR for analysis of gene-specific DNA methylation,Nucleic Acids Research, Jun. 8, 2005, 33(10), Oxford University Press.

Nisman, B., et al, The Follow-up of Patients with Non-muscle-invasive Bladder Cancer by Urine Cytology, Abdominal Ultrasound and Urine CYFRA 21-1:A Pilot Study, Anticancer Research, Oct. 2009, 29(10): 4281-4286, International Institute of Anticancer Research.

Li and Dahiya, MethPrimer: designing primers for methylation PCRs, Bioinformatics, Nov. 2002, 18(10): 1427-1431, Oxford University Press.

Sasaki, M., et al., Bisulfite conversion-specific and methylation-specific PCR: a sensitive technique for accurate evaluation of CpG methylation, Biochemical and Biophysical Research Communications, Sep. 19, 2003, 309(2): 305-309. Elsevier.

Mansoor, I., et al., Role of Urinary NMP-22 Combined with Urine Cytology in Follow-up Surveillance of Recurring Superficial Bladder Urothelial Carcinoma, Analytical and Quantitative Cytology and Histology, Feb. 2008, 30(1):25-32, The International Academy of Cytology and the Italian Society of Urologic Pathology.

Furichi, Y., et al.,Chemical modification of tRNAyeastTyr with bisulfite. A new method to modify isopentenyladenosine residue, Biochemical and Biophysical Research Communications, Dec. 1970, 41(5) 1185-1191, Elsevier.

* cited by examiner

DETECTING DNA METHYLATION OF BCL2, CDKN2A AND NID2 GENES TO PREDICT BLADDER CANCER IN HUMANS

CROSS-REFERENCE TO RELATED APPLICATION

The present application claims the benefit of priority under 35 U.S.C. §119(e) to U.S. Provisional Application No. 61/602,327 filed Feb. 23, 2012, the disclosure of which is hereby incorporated by reference in its entirety.

FIELD OF THE INVENTION

The present invention generally relates to identifying a panel of gene biomarker that undergoes DNA methylation on CpG islands and establishing its association with bladder cancer. Specifically, the present invention provides a method of detecting methylation status of BCL2, CDKN2A, and NID2 genes and using same to predict or diagnose bladder cancer in humans.

BACKGROUND OF THE INVENTION

Statistics from the American Cancer Society indicates that bladder cancer causes ~15,000 deaths in the United States and there are ~70,000 reported new cases annually (Siegel, Ward et al., 2011). If unchecked, bladder cancer may be lethal and the recurrent rate of bladder cancer is high. Thus early detection as well as regular monitoring for bladder cancer is recommended, ideally involving the use of non-invasive diagnostic techniques.

DNA methylation of multiple genes may contribute to the pathogenesis of bladder cancer. DNA methylation of many genes (e.g., 66 genes) has been reported in different bladder cancer patients. (See, e.g., Renard, Joniau et al., 2009). Many of the studies were performed using bladder tissues obtained from cancer patients, while others were performed using patient urine samples.

A number of different panels of genes have been reported to undergo DNA methylation associated with bladder cancer. For example, Friedrich et al. used quantitative methylation specific PCR and analyzed the apoptosis-related genes including ARF, FADD, TNFRSF21, BAX, LITAF, DAPK, TMS-1, BCL2, RASSF1A, TERT, TNFRSF25, and EDNRB. They reported DNA methylation of DAPK, BCL2 and TERT in 78% of urine samples of high stage bladder cancer patients. (Friedrich, Weisenberger et al., 2004). Vinci et al. reported 79% of the patients with bladder cancer exhibited DNA methylation of DAPK, TERT, and BCL2. (Vinci, Giannarini et al., 2009). Hogue et al. reported DNA methylation of four (4) genes (i.e., CDKN2A, ARF, MGMT, and GSTP1) with 69% sensitivity and 100% specificity. Using a two stage analysis, Hogue et al. reported promoter DNA hypermethylation of an additional five (5) genes (i.e., APC, CDH1, RAR β2, RASSF1A, and TIMP3) on samples that were tested negative for CDKN2A, ARF, MGMT, and GSTP1, and this additional test has a sensitivity of 82% and specificity of 96%. (Hogue, Begum et al., 2006). Renard et al. identified TWIST1 and NID2 to be frequently methylated based on an arbitrary cut-off value in urine samples collected from bladder cancer patients. (Renard, Joniau et al., 2009). Costa et al. identified GDF15, HSPA2, TMEFF2, and VIM as potential DNA methylation biomarkers for bladder cancer. (Costa, Henrique et al., 2010). Reinert et al. used the microarray approach and reported potential methylated CpG sites in ZNF154, POU4F2, HOXA9, and EOMES. Chung et al. applied the microarray approach and reported six methylation markers (namely, MYO3A, CA10, SOX11, NKX6-2, PENK, and DBC1) in urine sediments of bladder cancer patients. (Chung, Bondaruk et al., 2011)

It is noteworthy that a quantitative DNA methylation assay provides a measurement of how much DNA methylation occurs (i.e., the assay provides copy numbers of the methylated gene panel). However, quantitative DNA methylation measurement is often arbitrary because the level of DNA methylation of a gene in a bladder cancer patient is in comparison to the same gene from a healthy individual. The DNA methylation level is based on an arbitrary set cut-off in those healthy individuals. Depending on the cut-off values, the quantitative assays lack consistency and contain small allowances for error in obtaining the reported sensitivities and specificities.

There still exists a continuing need in searching a panel of genes that exhibit DNA methylation associated with bladder cancer. There is also a need to utilize a non-invasive test to detect DNA methylation of such gene panel in order to serve as biomarkers in monitoring an increased risk (in occurrence) of bladder cancer. The present inventors have successfully identified the DNA methylation of a panel of BCL2, CDKN2A and NID2 genes as biomarkers of bladder cancer.

SUMMARY OF THE INVENTION

In one aspect, the present invention provides a method of determining an increased occurrence (i.e., increased risk) of bladder cancer in a human, comprising the steps of: (a) obtaining a urine sample from a human; (b) isolating genomic DNA from said urine; (c) exposing said isolated genomic DNA with sodium bisulfite; (d) performing a first round PCR on said sodium bisulfite-treated genomic DNA to amplify a methylation site present on a CpG island, said CpG island is present on a plurality of genes consisting of BCL2, CDKN2A, and NID2; (e) performing a second round PCR to detect DNA methylation status on said methylation site; and (f) determining an increased risk of bladder cancer in said human, wherein the detection of DNA methylation status on said CpG island of said plurality of genes in said urine sample is indicative of an increased risk of bladder cancer in said human.

In another aspect, the present invention provides a method of determining an increased risk of bladder cancer in a human, comprising the steps of: (a) obtaining a urine sample from a human; (b) isolating genomic DNA from said urine; (c) exposing said isolated genomic DNA with sodium bisulfite; (c') performing a real time PCR to amplify β-actin on said sodium bisulfite-treated genomic DNA, wherein a Ct value of ≤25 is indicative of a sufficient amount of sodium bisulfite treated genomic DNA in said urine; (d) performing a first round PCR on said sodium bisulfite-treated genomic DNA to amplify a methylation site present on a CpG island, said CpG island is present on a plurality of genes consisting of BCL2, CDKN2A, and NID2; (e) performing a second round PCR to detect DNA methylation status on said methylation site; and (f) determining an increased risk of bladder cancer in said human, wherein the detection of DNA methylation status on said CpG island of said plurality of genes in said urine sample is indicative of an increased risk of bladder cancer in said human.

In another aspect, the second round PCR is a nested methylation-specific assay.

In another aspect, the first round PCR is performed using a forward primer and a reverse primer for BCL2, CDKN2A, and NID2 respectively. The forward primers having a nucleotide sequence consisting of SEQ ID NO: 1 (for BCL2), SEQ ID NO: 5 (for CDKN2A), and SEQ ID NO: 7 (for NID2). The reverse primers having a nucleotide sequence consisting of SEQ ID NO: 2 (for BCL2), SEQ ID NO: 6 (for CDKN2A), and SEQ ID NO: 8 (for NID2).

In another aspect, the second round PCR is performed using a forward primer and a reverse primer for BCL2, CDKN2A, and NID2 respectively. The forward primers having a nucleotide sequence consisting of SEQ ID NO: 9 (for BCL2), SEQ ID NO: 15 (for CDKN2A), and SEQ ID NO: 18 (for NID2). The reverse primers having a nucleotide sequence consisting of SEQ ID NO: 10 (for BCL2), SEQ ID NO: 16 (for CDKN2A), and SEQ ID NO: 19 (for NID2).

In another aspect, the second round PCR is performing using a probe for BCL2, CDKN2A, and NID2 respectively. The probe having a nucleotide sequence consisting of SEQ ID NO: 11 (for BCL2), SEQ ID NO: 17 (for CDKN2A) and SEQ ID NO: 20 (for NID2).

In another aspect, the first round PCR for β-actin is performed using a forward primer and a reverse primer for β-actin. The forward primer having a nucleotide sequence of SEQ ID NO: 3, and the reverse primer having a nucleotide sequence of SEQ ID NO: 4 (for BCL2).

In another aspect, the second round PCR for β-actin is performed using a forward primer and a reverse primer for β-actin. The forward primer having a nucleotide sequence of SEQ ID NO: 12, and the reverse primer having a nucleotide sequence of SEQ ID NO: 13.

In another aspect, the second round PCR for β-actin is performing using a probe for β-actin. The probe having a nucleotide sequence of SEQ ID NO: 14.

In another aspect, the present invention provides a method of diagnosing a low malignant potential bladder cancer in human, comprising the steps of: (a) obtaining a urine sample from a human; (b) isolating genomic DNA from said urine; (c) exposing said isolated genomic DNA with sodium bisulfite; (d) performing a first round PCR on said sodium bisulfite-treated genomic DNA to amplify a methylation site present on a CpG island, said CpG island is present on a plurality of genes consisting of BCL2, CDKN2A, and NID2; (e) performing a second round PCR to detect DNA methylation status on said methylation site; and (f) determining an increased risk in bladder cancer in said human, wherein the detection of DNA methylation status on said CpG island of said plurality of genes in said urine sample is indicative of an increased risk of bladder cancer in said human. Preferably, the low malignant potential bladder cancer is transitional cell carcinoma.

BRIEF DESCRIPTION OF THE FIGURES

Embodiments of the invention are herein described, by way of non-limiting example, with reference to the following accompanying figures.

DETAILED DESCRIPTION OF THE INVENTION

Definitions

Figure 1:
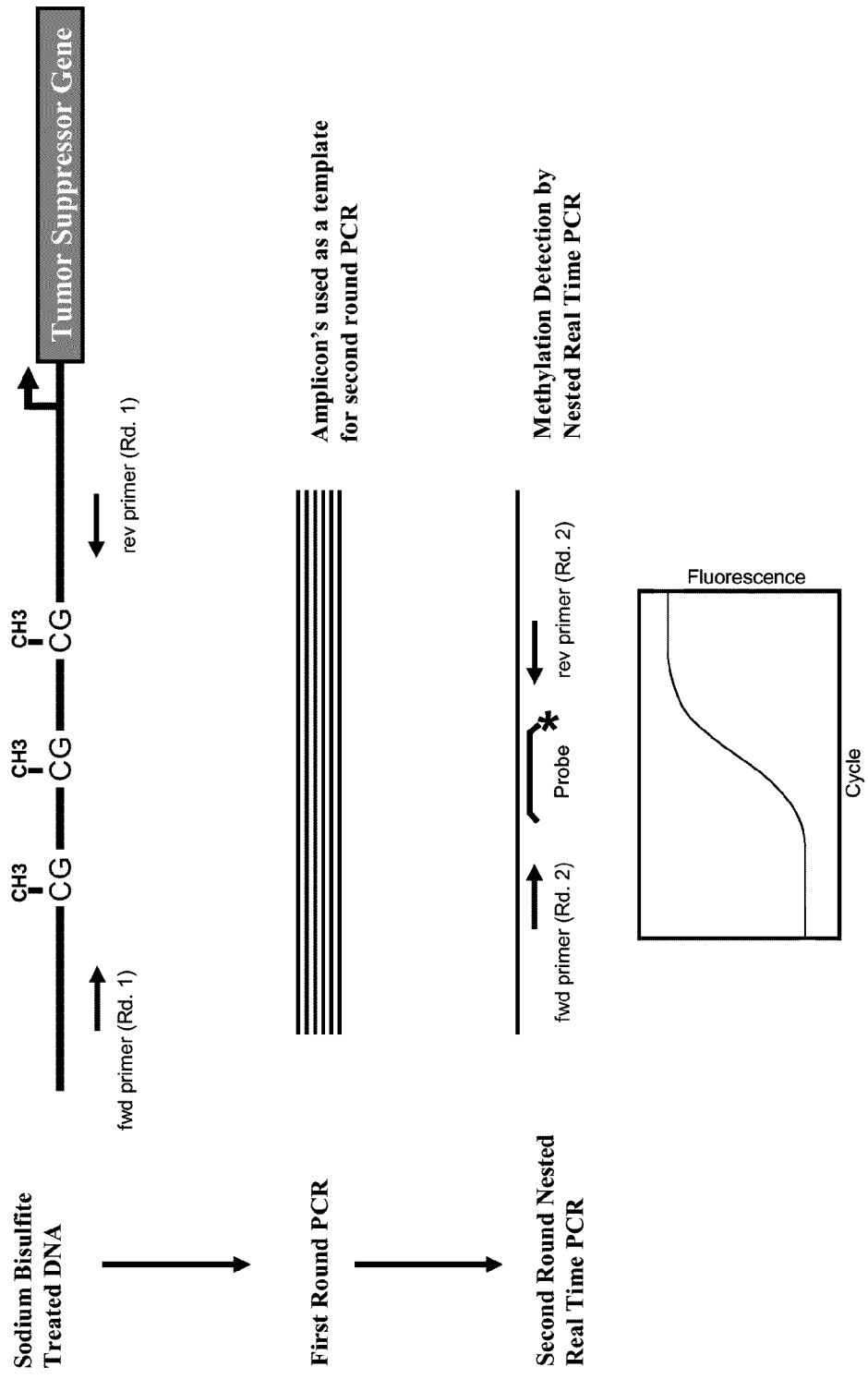
FIG. 1 depicts the process of DNA methylation detection of BCL2, CDKN2A, and NID2.

Various terms used throughout this specification shall have the definitions set forth herein.

As used herein, the term "CpG" island refers to a genomic region that contains a high frequency of CpG sites. "C" and "G" refer to cytosine and guanine, respectively. "p" refers to the phosphodiester bond between the cytosine and the guanine, which indicates that the C and the G are next to each other in sequence. A CpG island is characterized by CpG dinucleotide content of at least 60% of that which would be statistically expected (~4-6%), whereas the rest of the genome has a much lower CpG frequency (~1%).

As used herein, the term "methylation site" when used in the context of a CpG island refers to a site where a C is immediately followed by a G that is present on a CpG island.

As used herein, the term "genomic DNA" refers to DNA found within the 46 chromosomes in humans. The genomic DNA provides a complete set of genetic information including coding and non-coding DNA.

As used herein, the term "sodium bisulfite" refers to sodium hydrogen sulfite having the chemical formula of $NaHSO_3$. Sodium bisulfite functions to deaminate cytosine into uracil; but does not affect 5-methylcytosine (a methylated form of cytosine with a methyl group attached to carbon 5). When the bisulfite-treated DNA is amplified via polymerase chain reaction, the uracil is amplified as thymine and the methylated cytosine is amplified as cytosine.

As used herein, the term "methylation" refers to the addition of a methyl group to the 5' carbon of the cytosine base in a deoxyribonucleic acid sequence of CpG within a gene on a human chromosome.

As used herein, the term "methylation status" refers to the presence or absence of a methylated cytosine base at a methylation site in a CpG island within a gene. Methylation of a CpG island is often associated with inhibition of gene expression. A CpG island often begins upstream of a gene in the promoter. For purposes of this application, a CpG island can span the promoter region, the coding region (e.g., exons), and the non-coding region (e.g., introns) of a gene.

As used herein, the term "methylation specific PCR" refers to the use of primer pairs in a PCR reaction that are complimentary to DNA that is converted by sodium bisulfite and that contains several CpG dinucleotides (i.e., multiple methylation sites) that can be methylated in vivo. Primers can be complimentary to the methylated template where methylated CpG cytosines are not converted to uracil by the sodium bisulfite treatment and non-CpG cytosines are converted to uracil.

As used herein, the term "nested PCR" refers to a variation of the polymerase chain reaction (PCR) in that two pairs of PCR primers are used to amplify a fragment. The first pair of PCR primers amplifies a portion of a gene to form a first amplicon. The second pair of primers is nested within the first amplicon and bind inside the first amplicon to allow amplification of a second amplicon which is shorter than the first amplicon.

As used herein, the term "real time PCR" (also called quantitative real time polymerase chain reaction) refers to a method for the detection and quantitation of an amplified PCR product based on incorporation of a fluorescent reporter dye; the fluorescent signal increases in direct proportion to the amount of PCR product produced and is monitored at each cycle, 'in real time', such that the time point at which the first significant increase in the amount of PCR product correlates with the initial amount of target template.

As used herein, the term "primer set" refers to a pair of PCR primers that include a forward primer and reverse primer used in a PCR reaction and allows the generation of an amplicon.

As used herein, the term "probe" refers to a TaqMan probe used in a real time PCR and it consists of a fluorophore covalently attached to the 5'-end of an oligonucleotide designed such that it anneals within a DNA region amplified by a specific set of primers and a quencher at the 3'-end. The quencher molecule quenches the fluorescence emitted by the fluorophore when excited by a light source via FRET (Fluorescence Resonance Energy Transfer). As the Taq polymerase extends the primer during PCR and synthesizes the nascent strand the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore.

As used herein, the term "detecting the methylation status of a gene" refers to detecting or assessing the presence or absence of a methylated cytosine base in a CpG island within a gene of interest. Methods of detecting the methylation status of a gene include, for example, nested methylation specific PCR, methylation specific PCR or bisulfite sequencing.

As used herein, the term "BCL2" refers to Bcl-2 (i.e., B-cell lymphoma 2), which is the founding member of the Bcl-2 family of apoptosis regulator proteins. The nucleotide sequence is deposited in a GenBank database with NCBI Reference Sequence: NM_000633.2, the disclosure of which is incorporated herein by reference.

As used herein, the term "CDKN2A" refers to cyclin-dependent kinase inhibitor 2A, which is a tumor suppressor protein that plays an important role in regulating the cell cycle. The nucleotide sequence is deposited in a GenBank database with NCBI Reference Sequence: NM_000077.4, the disclosure of which is incorporated herein by reference.

As used herein, the term "NID2" refers to Nidogen-2, which is a basement membrane protein in humans. The nucleotide sequence is deposited in a GenBank database with NCBI Reference Sequence: NM_007361.3, the disclosure of which is incorporated herein by reference.

As used herein, the term "ACTB" refers to β-actin, which is one of six different actin isoforms which have been identified in human/s. The nucleotide sequence is deposited in a GenBank database with NCBI Reference Sequence: NM_001101.3, the disclosure of which is incorporated herein by reference.

As used herein, the term "grade" describes the intrinsic aggressive potential of a bladder cancer.

As used herein, the term "stage" describes the extent to which a cancer has invaded into the patient tissue from the bladder wall. For example, a superficial bladder cancer diagnosis based on stage is a cancer found only on the surface of the inner lining of the bladder.

As used herein, the term "increased risk of bladder cancer" refers to an increase in the occurrence of bladder cancer in patients as compared to the occurrence of bladder cancer in healthy individuals. Healthy individuals have a negligible occurrence of bladder cancer (i.e., <0.04%) (Siegel et al., 2001). The present inventors establish a correlation between positive DNA methylation status in CpG islands on specific genes and an increase in occurrence of bladder cancer in patients. In other words, the present DNA methylation assay reveals a positive predictive value of 91.8% (i.e., 91.8% of all the patients who tested positive DNA methylation status would suffer from bladder cancer).

As used herein, the term "Low malignant potential" refers to Papillary urothelial neoplasm of low malignant potential (PUNLMP), which is a bladder cancer that is slow growing and unlikely to spread. It is the lowest grade of bladder cancer.

As used herein, the term "Low Grade" refers to Low grade papillary urothelial carcinoma, which is a bladder cancer that is slow growing and unlikely to spread, but is more likely to recur and progress compared with low malignant potential.

As used herein, the term "High Grade" refers to High grade papillary urothelial carcinoma, which is a bladder cancer that is more quickly growing and more likely to spread as compared with low grade tumors and low malignant potential tumors.

As used herein, the term "transitional carcinoma cell" refers to a malignant tumor arising from a transitional type of stratified epithelium, and affecting the urinary bladder. This represents the most common form of bladder cancer and accounts for greater than 90% of the bladder cancer patients.

The present invention provides a method of detecting DNA methylation (i.e., detecting DNA methylation status) in urine of a plurality of genes including BCL2, CDKN2A, and NID2. An increase in DNA methylation of these genes is found to be correlated with bladder cancer. The present method comprises a step of obtaining urine samples collected from a human suspected of having a bladder cancer, isolating DNA from urines, followed by treating the isolated DNA with a chemical agent (such as sodium bisulfite) to convert unmethylated cytosine to uracil present within CpG islands near gene promoters. The DNA methylation near the gene promoter is detected using a two round PCR protocol. The first round PCR amplifies DNA regions of interest that undergo DNA methylation, and the second round PCR is a nested methylation-specific PCR. Together, the present invention provides a DNA methylation detection assay that offers good sensitivity and specificity. The present DNA methylation assay offers an optimal test to predict low-grade bladder cancer.

Bladder cancer has a high cancer recurrence rate. As such, bladder cancer patients require regular monitoring, often with invasive diagnostic techniques. It would be ideal to develop a specific non-invasive assay that would promote patient compliance with a monitoring program. Other diagnostic tests are commercially available for bladder cancer detection, including for example, the UroVysion™ assay provided by Abbot Molecular. To the best of the present inventors' knowledge, there is no DNA methylation assay that is commercially available for bladder cancer detection. There have been reported that DNA methylation can be detected from tumor cells that are potentially shed from the bladder wall into urine. A majority of these assays involving DNA methylation involves single round quantitative methylation-specific Real Time PCR. Many of these reported studies result in high Ct values (i.e., >30), evidencing a low and sub-optimal sensitivity, one that is not commercially viable.

The present invention provides obtaining urine from patients suspected of having bladder cancer. Urine is easily attainable as a biological sample. Urine DNA (i.e., genomic DNA) is prepared and DNA methylation for specific genes of the isolated urine DNA is determined so as to predict the incidence of bladder cancer. In one embodiment, urine is collected optimally between 5 mL to 50 mL that is sufficient for isolation of between 0.1 μg to 2 μg of DNA (i.e., genomic DNA in urine) and measurement of DNA methylation. Urine collection protocol is well recognized by one skilled in the art, such as urine collection with a collection cup. Voided urine can be collected at any convenient time during the day including morning or evening. In one embodiment, freshly collected urine may be used for DNA methylation assay. In another embodiment, collected urine may be frozen immediately and stored at a preferred temperature range of −20° to −80° C.

The present invention provides for isolating the genomic DNA from urine. In one embodiment, urine may be briefly centrifuged (e.g., 4,000 rpm, 5 minutes) to spin down any pellets (i.e., sediments). The prepared urine pellets are found to contain DNA (i.e., nucleic acids). The prepared urine pellets also may contain cellular debris as well as protein contaminants that can be eliminated by treating the pellets with a lysis solution. (See, e.g., Sambrook, J., et al., *Molecular cloning*: A Laboratory Manual, (2001) 3rd edition, Cold Spring Harbor Laboratory Press, Cold Spring Harbor, N.Y.). In one embodiment, the lysis solution contains a mixture of SDS (1%) and proteinase K (e.g., 5-120 μg/mL, 4-16 hours). Treatment with lysis solution may be performed at an optimal temperature range of 37° C.-56° C., preferably at 42° C. After the lysis treatment, genomic DNA is extracted. One skilled in the art would recognize numerous DNA extraction protocols. In one embodiment, DNA is extracted using a mixture of phenol and chloroform. Preferably, the mixture contains 50% phenol, 48% chloroform, and 2% isoamyl alcohol. Commercially available purification kits (for genomic DNA isolation) may also be used. During the DNA extraction procedure, degraded protein contaminants as well as cell debris are removed.

To detect DNA methylation of a particular region of genomic DNA associated with a gene that contains a CpG island, the present method provides for first converting the isolated genomic DNA so that the majority of unmethylated cytosine is converted to uracil. In one embodiment, a chemical reagent that selectively modifies either the methylated or non-methylated form of CpG dinucleotide motifs may be used. Suitable chemical reagents include hydrazine and bisulphite ions and the like. Preferably, isolated DNA is treated with sodium bisulfite ($NaHSO_3$) which converts unmethylated cytosine to uracil, while methylated cytosines are maintained (Furuichi et al., 1970). Without wishing to be bound by a theory, it is understood that sodium bisulfite reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonated group can be removed under alkaline conditions, resulting in the formation of uracil. It is generally understood that sodium bisulfite treatment causes the conversion of the majority of unmethylated cytosine to uracil within the CpG islands of a specific gene. The nucleotide conversion results in a change in the sequence of the original DNA. It is general knowledge that the resulting uracil has the base pairing behavior of thymine, which differs from cytosine base pairing behavior. To that end, uracil is recognized as a thymine by Taq polymerase. Therefore after PCR, the resultant product contains cytosine only at the position where 5-methylcytosine occurs in the starting template DNA. This makes the discrimination between unmethylated and methylated cytosine possible. Useful conventional techniques of molecular biology and nucleic acid chemistry for assessing sequence differences are well known in the art. (See, for example, Sambrook, J., et al., *Molecular cloning*: A laboratory Manual, (2001) 3rd edition, Cold Spring Harbor, N.Y.).

The present inventors develop an optimal cancer detection using DNA methylation. Although DNA methylation is sensitive and specific, it may be difficult to utilize this test to detect bladder cancer. This is so because there is a limited number of tumor cells present in urine. It is hypothesized, that because of the disproportionate high numbers of healthy cells relative to low numbers of tumor cells in urine, that a highly sensitive DNA methylation assay is required to detect bladder cancer in urine. This is so especially during the early stage of bladder cancers. If the selected CpG island present in a gene is methylated in a few cancer cells, any methylation activity from the thousands of healthy cells may affect the background signals (i.e., high background noise). This is consistent with the high cutoff values for DNA methylation from healthy urine samples in many reported studies (see, i.e., Renard, Joniau et al. 2009).

It remains a difficult task to select a panel of genes that undergo DNA methylation and is restricted to bladder cancer patients. The present inventors selected a novel panel of genes containing BCL2, CDKN2A, and NID2 that represents an improved panel over those reported in the prior art. The present invention provides detection of DNA methylation using this panel of genes and the DNA methylation assay unexpectedly has a high sensitivity and specificity for detecting bladder cancer cells, but not healthy cells that are present in urine (i.e., panel provides low background noise).

The present invention provides a method of detecting DNA methylation using a plurality of specific genes. It is discovered that DNA methylation of BCL2 and NID2 sufficiently provides a high sensitivity of >76% and a specificity of >91%. It is further discovered that DNA methylation of CDKN2A (in addition to BCL2 and NID2) further increases its sensitivity to >81% and a specificity of >86%.

It is recognized by clinicians that it is crucial to detect bladder cancer before the cancer reaches a high grade and migrate aggressively into other areas. It is also recognized that detection of such a cancer would allow better treatment before the cancer may reach to a higher grade. However, detection of a bladder cancer while it is at a low malignant potential grade is a difficult task. It is hypothesized that a low malignant potential tumor cell has less methylation as compared to that of high grade. The less methylation accounts for the difficulty for its detection using a methylation assay. The present invention provides a method of detecting DNA methylation for CDKN2A gene, together with BLC2 and NID2 genes. The selected gene combination surprisingly offers a high sensitivity for detecting low malignant potential bladder cancers. In low malignant bladder cancers, the DNA methylation assay of BCL2 and NID2 provides a sensitivity of >36% and a specificity of >91%. The present inventors discovered that DNA methylation of CDKN2A, in combination with BCL2 and NID2, surprisingly increases the sensitivity from 36% to 55%.

In one embodiment, the present DNA methylation method provides a two round (i.e., two step) PCR reactions for detecting the methylation status of the BCL2, CDKN2A, and NID2 genes. The present two-step PCR is an improved methylation assay that provides a much higher sensitivity and specificity for detecting DNA methylation.

In the first round PCR reaction, primer sets (i.e., forward primer and reverse primer) are designed to flank the methylation sites of interest (i.e., potential methylation sites) that are present on a CpG island of a particular gene (e.g., BCL2). Preferably, primers are designed to anneal to non-CpG containing regions within the specific CpG island of that particular gene. After the first round PCR, the resulting amplicon contains CpG dinucleotides that are aberrantly methylated. The amplicon generated from first round PCR reaction thus provides a template for the second round PCR reaction which then detects the methylation status of the respective genes.

In the second round PCR reaction (i.e., nested methylation specific PCR), its primer sets (i.e., forward primer and reverse primer) are designed to perform as a nested methylation specific PCR reaction. The second PCR amplifies the region within the amplicon (generated from the first round PCR reaction) that contains the methylation sites of interest. Therefore, the second round PCR uses the first round amplicon as a template for the PCR reaction. The second round PCR uses primer sets that are methylation specific primers. The methylation specific primers are designed to locate internally within the flanking primers of the first round PCR.

For purposes of the present invention, particular genes are selected to identify their methylation status in order to determine their usefulness in predicting bladder cancer. The present inventors have successfully identified the BCL2, CDKN2A, and NID2 genes which methylation status can be used as a biomarker for predicting bladder cancer.

Using publically available genomic sequence databases (e.g., genome browser provided by UCSC, http://genome.ucsc.edu/index.html) the location of the CpG island for a particular gene is determined. For example, BCL2 gene is located on human chromosome 18 between base pairs 60,790,579 and 60,986,613, the nucleotide sequence of which is deposited in the GenBank database with NCBI Reference Sequence: NM_000633.2. The transcriptional start site of the BCL2 gene is at the base pair 60,986,613. The CpG island on the BCL2 gene is located on chromosome 18 between base pairs 60,985,504 and 60,985,741. CDKN2A gene is located on human chromosome 9 between base pairs 21,967,751 and 21,994,490, the nucleotide sequence of which is deposited in the GenBank database with NCBI Reference Sequence: NM_000077.4. The transcriptional start site of the CDKN2A gene is at the base pair 21,994,490. The CpG island on the CDKN2A gene is located on chromosome 9 between base pairs 21,974,579 and 21,975,306. NID2 gene is located on human chromosome 14 between base pairs 52,471,520 and 52,535,946, the entire nucleotide sequence of which is deposited in the GenBank database with NCBI Reference Sequence: NM_007361.3. The transcriptional start site of NID2 gene is at the base pair 52,535,946. The CpG island on the NID2 gene is located on chromosome 14 between base pairs 52,534,582 and 52,536,722. β-actin gene is located on human chromosome 7 between base pairs 5,566,779 and 5,570,232, the nucleotide sequence of which is deposited in the GenBank database with NCBI Reference Sequence: NM_001101.3. The transcriptional start site of the β-actin gene is at the base pair 5,570,232. The CpG island on the β-actin gene is located on chromosome 7 between base pairs 5,569,063 and 5,670,594. The disclosure of all of which are incorporated herein by references.

It is known in the field that there are many methylation sites that are present on a CpG island with respect to a particular gene. A methylation site is characterized by having a cytosine (C) is followed by a guanine (G) that are present within a CpG island. It is also recognized by one skilled in the art that a majority of methylation sites (present within a CpG island of a particular gene) are unmethylated in healthy cells. During cancer development, these methylation sites within a CpG island undergo DNA methylation.

In one embodiment, the present invention provides a method of using bisulfite sequencing to identify "real" methylation sites present on a CpG island (i.e., methylated CpG only in cancer cells but not in healthy cells). The protocol of bisulfite sequencing is known by one skilled in the art. In short, isolated DNA (from urine) is treated with sodium bisulfite followed by a sequencing reaction to provide information relating to the locations of methylated CpG dinucleotides present within a CpG island. Primer sets for sequencing reaction with respect to the three (3) genes (i.e., BCL2, CDKN2A and NID2) can be designed.

Once the methylation sites present on a CpG island for a particular gene is determined, the second round primer sets can be designed prior to that of the first round primer sets. Primer sets can be conveniently synthesized and purified using standard technology known in the art. Design of primer sets for the second round PCR can be performed using the following guidelines.

First, the second round PCR primers (i.e., forward primer and reverse primer) must anneal to sufficient number of CpG so as to be methylation specific. Methylation specific primers can be conveniently designed to amplify regions within the CpG island. In one embodiment, at least ≥3 CpG are required for the annealing to occur. The sufficient number of CpG is required so that when non-methylated CpG are converted to uracil (by sodium bisulfite treatment), the mismatches (between primers and CpG) are sufficient to prevent hybridization of the second round primers. It has been determined that a mismatch of only a single uracil (i.e., containing only one (1) CpG) may still allow the second round primer to anneal and amplify to yield an amplicon. Primers may be verified for such DNA methylation specificity. To do so, PCR reactions may be compared between sodium bisulfite treated DNA that is unmethylated and sodium bisulfite treated DNA that is methylated. Products of a PCR reaction (i.e., amplicons) may be detected using gel electrophoresis (e.g., agarose or polyacrylamide gel). An amplicon product may be visualized with a specific dye (e.g., ethidium bromide) that would intercalate into double-stranded DNA and provides visualisation of the DNA bands under a UV illuminator. Other detection means includes, for example, hybridization of the PCR amplification products with an oligonucleotide probe.

Second, the second round PCR primer must be bisulfite specific. It has been determined that the second round PCR primers must hybridize to ≥4 cytosines not followed by guanine (i.e., non-CpG cytosine) that will be converted to uracil (following sodium bisulfite treatment). These cytosines cannot be methylated and will always be converted to uracil after sodium bisulfite treatment. If there are less than four (4) non-CpG cytosines, second round PCR primers may hybridize to DNA not fully converted by sodium bisulfite and therefore false positive results may occur.

Third, the second round PCR primers must amplify to yield an optimal length of amplicon so as to maintain good PCR efficiency. Preferably, an optimal amplicon length is between ≥about 80 base pairs and ≤about 150 base pairs. There is an inverse relationship between the amplicon length and PCR efficiency. The underlying rationale is related to the fact that sodium bisulfite treatment often causes degradation of DNA and therefore PCR efficiency decreases as amplicon size gets larger. Consideration also is given to the fact that a smaller amplicon resulting from the second round PCR amplicon allows adequate room for designing the first round primers.

Fourth, the second round PCR primers have a melting temperature (i.e., $T_M$) of ~60° C. This $T_M$ range provides adequate annealing of the second round primers to its template and extension of the PCR product simultaneously during a real time PCR.

Primer sets for the second round PCR may be conveniently designed with the assistance of a computer. An exemplary computer program includes MethPrimer (Li and Dahiya, 2002). After the nucleotide sequence of the entire CpG island of a particular gene is entered into the computer. The computer program scans the nucleotide sequence of the CpG island of the gene, and provides primer sets for methylation specific PCR reaction. The computer program establishes several criteria for designing methylation specific PCR primers, including for example—(i) the numbers of CpG dinucleotides that each primer set would hybridize (higher CpG numbers offers better discrimination between methylated vs. unmethylated CpG); (ii) presence of non-CpG cytosine; (iii) melting temperature for each primer set (e.g., ~60° C.) for real-time PCR; (iv) to achieve an optimal amplicon size for real time PCR (e.g., between 80-150 base pairs).

For detecting DNA methylation of the three (3) genes (i.e., BCL2, CDKN2A and NID2), the second round PCR requires three (3) primer sets respective for each particular gene.

It is therefore a feature of the present invention that the primers used in the second round PCR is a nested PCR amplification as well as methylation specific (i.e., the primers contain CpG dinucleotides that are potentially methylated and the primers only hybridize to the sites of interest when those CpG dinucleotides are methylated and therefore not converted to uracil by sodium bisulphate).

In one embodiment, primers sets used in the second round PCR include: (i) BCL2: SEQ ID NO: 9 (forward primer) or SEQ ID NO: 10 (reverse primer); (ii) CDKN2A: SEQ ID NO: 15 (forward primer) or SEQ ID NO: 16 (reverse primer); (iii) NID2: SEQ ID NO: 18 (forward primer) or SEQ ID NO: 19 (reverse primer).

In another embodiment, the second round PCR is a real-time quantitative methylation specific PCR. This assay provides a continuous optical monitoring of an amplification procedure and utilizes fluorescently labeled reagents whose incorporation into the amplified product can be quantified. The quantification of an amplified product is indicative of the copy number of that sequence in the template. An exemplary fluorescent dye includes SYBR Green. Other labeled probes may also be used for quantification in accordance with techniques that are known in the art (such as TaqMan™, Molecular Beacons™ and the like). Real Time TaqMan™ assay adds to the specificity in detecting DNA methylation. This is because annealing of the probe to the DNA template is dependent upon the DNA template containing sites of DNA methylation (i.e., amplification is seen only when the methylation specific forward and reverse primers can anneal to the template, as well as the probe).

In the present invention, methylation specific TaqMan™ probes may be used in the detection to visualize the amplification of methylated DNA. Probes that hybridize to the DNA templates for the second round primers are designed by selecting a region between the second round primer sets (i.e., forward and reverse primers) that depend on the following criteria: (i) the numbers of CpG that the probe would hybridize (e.g., ~3° C.); (ii) presence of non-CpG cytosine (e.g., ~4 cytosines); (iii) melting temperature for each primer set (e.g., ~65° C.). Preferably, the annealing/extension temperature during the PCR reaction is between about 60° C. and about 65° C. In one embodiment, probes used in the second PCR respectively include: (i) BCL2: SEQ ID NO: 11; (ii) CDKN2A: SEQ ID NO: 17; and (iii) NID2: SEQ ID NO: 20.

For sake of convenience, primer design for the first round PCR is performed after selection of the second round PCR primers in the present invention. Primers for the first round of PCR are selected by scanning the nucleotide sequence surrounding the location of the second round PCR primers for sequences that will allow generation of first round amplicons. Accordingly, first round primers must flank the second round PCR primers.

In addition, the first round primers are selected based, in part, on the following criteria. First, the size of the first round PCR products (i.e., amplicon) is in the range of about ≤350 base pairs. Optimally, the first round PCR primers amplify first round amplicons that are ~50 base pairs outside the second round PCR 5' ends. Primers generating amplicons larger than this range will be difficult to generate due to fragmentation of DNA present in urine as well as fragmentation caused by sodium bisulfite treatment.

Second, the first round primers are DNA methylation independent. The primers contain no CpG sites in the primer sequence. In other words, primer sets for the first round PCR are specifically designed to exclude CpG dinucleotides. The CpG dinucleotides exclusion is to permit DNA amplification that is independent of the methylation status of potential DNA methylation that could occur on CpG sites not of interest within a primer. Therefore, all methylated and unmethylated DNA sequences internal to the binding sites of the primers are co-amplified for any given gene by a single set of flanking primers specific for that gene. The flanking primer pair for a gene being investigated is complimentary to two sequences; one upstream and one downstream of the CpG sites that are to be queried in a second round nested methylation specific PCR.

Third, the first round PCR primers must be bisulfite specific. The first round primers must hybridize to ≥4 cytosines. These cytosines are not followed by guanine (i.e., non-CpG cytosines). In other words, these cytosines cannot be methylated and will always be converted to uracil after bisulfite treatment. Primers that are not bisulfite specific (i.e., hybridize to less than 4 non-CpG cytosines) may hybridize to DNA that are not fully converted by sodium bisulfite and thus resulting in false positive results.

Fourth, the melting temperature for the first round PCR primers should be less than that of the second round PCR primer. In one embodiment, the melting temperature for each primer set in the range of ~45-55° C.

Fifth, the first round PCR primer does not anneal at the annealing temperature of the second round PCR reaction. If the first round primers anneal at the annealing temperature of the second round PCR reaction, the result would be a false positive result due to a loss of methylation specificity in the second PCR.

Sixth, the first round PCR primers should avoid (i) a consecutive of >3 cytosines, or (ii) a consecutive of >3 cytosines and thymines in combination. Such consecutive cytosines or cytosines/thymines will both be recognized as thymines after cytosines are converted to uracils following bisulfite treatment. In the event that there are >3 consecutive cytosines or cytosines/thymines, it would force the first round PCR primers to contain a consecutive >3 adenines. These PCR primers would suffer from (i) a low annealing temperature, (ii) a decrease in specificity (i.e., non-specific PCR).

In accordance with the present invention, first round PCR primers should have a sufficiently high annealing temperature so that any annealing of mismatch of the primers to a non-specific sequence of DNA would not occur. Thus, a sufficiently high annealing temperature would avoid production of a non-specific amplicon.

In accordance with the present invention, the first round PCR amplifies the DNA region within CpG islands. DNA methylation can be detected within these amplified CpG islands and can provide a high efficiency for methylation detection. For purposes of this application, the first round PCR often yield at least 100 fold amplification of the DNA regions within CpG islands. It is estimated that copy number of the methylated CpG islands is approximately in the range of 1-100 copies present in urine. It is also estimated that (after the first round PCR) copy number of the methylated CpG islands is approximately in the range of 100-10,000 copies present in urine.

The first round PCR (i.e., generation of the first amplicons) is a standard PCR reaction for the respective genes. However, each of the first round PCR reaction must use a hot start Taq DNA polymerase. In addition, the annealing temperature of the first round PCR is about 5-15° C. higher than the $T_M$ of the first round PCR primer sets. For example, with respect to the BCL2 gene, the annealing temperature for the first round PCR is 54° C., which is ~9° C. higher than the $T_M$ of the average first round PCR primer sets for BCL2 (i.e., ~45° C.). With respect to the CDKN2A gene, the annealing temperature for the first round PCR is 56° C., which is ~5° C. higher than the $T_M$ of the average first round PCR primer sets for CDKN2A (i.e., ~51° C.). With respect to the NID2 gene, the annealing temperature for the first round PCR is 56° C., which is ~6° C. higher than the $T_M$ of the average first round PCR primer sets for NID2 (i.e., ~50° C.). With respect to the control β-actin gene, the annealing temperature for the first round PCR is 54° C., which is ~7.5° C. higher than the $T_M$ of the average first round PCR primer sets for β-actin (i.e., ~46.5° C.).

The present invention provides first round primer sets for each of the three (3) selected genes (i.e., BCL2, CDKN2A and NID2). In one embodiment, first round PCR primer sets include: (i) BCL2: SEQ ID NO: 1 (forward primer) and SEQ ID NO: 2 (reverse primer); (ii) CDKN2A: SEQ ID NO: 5 (forward primer) and SEQ ID NO: 6 (reverse primer); and (iii) NID2: SEQ ID NO: 7 (forward primer) and SEQ ID NO: 8 (reverse primer).

In additional to the two round PCR methodology, other methylation detection techniques may be used for the present invention. One of ordinary skilled in the art recognizes that there are many existing techniques for determining methylation status of genes (i.e., BCL2, CDKN2A and NID2). For example, methylation assays include, but are not limited to, sequencing, methylation-specific PCR (MS-PCR), melting curve methylation-specific PCR, MLPA with or without bisulphite treatment, MSRE-PCR (Melnikov et al, 2005), bisulphite conversion-specific methylation-specific PCR (BS-MSP) (Sasaki et al., 2003), and the like. A review of techniques for determining DNA methylation analysis is provided in *Nucleic Acids Research,* 1998, Vol. 26, No. 10, 2255-2264, and *Nature Reviews,* 2003, Vol. 3, 253-266, the disclosure of which are incorporated herein by reference in their entirety.

In one aspect, the present invention provides the use of β-actin (i.e., ACTB) as a control. Using the two round PCR amplification protocol (described above), the β-actin amplification provides confirmatory information regarding the presence of sufficient genomic DNA in the urine (e.g., >10 ng). Such information is essential for the interpretation of the methylation status of genes in the present invention. If there is β-actin amplification (Ct<25 from the two round PCR assay), it indicates a sufficient amount of genomic DNA present in the urine. If there is no β-actin amplification (Ct>25 from the two round PCR assay), it indicates that there is insufficient amount of genomic DNA. The DNA methylation status cannot provide a correlation with respect to the occurrence (i.e., increased risk) of bladder cancer if there is no β-actin amplification (i.e., the assay potentially yields a false negative).

Similar to the BCL2, CDKN2A and NID2 genes, the present inventors use the two round PCR assay for β-actin. The two round PCR of the present invention is shown to provide high sensitivity and specificity towards detecting the gene methylation of BCL2, CDKN2A and NID2. The same two round PCR protocol is similarly adopted for the control β-actin in order to achieve the same sensitivity and specificity.

In accordance with the present invention, β-actin amplification is expected to occur in genomic DNA obtained from urine irrespective of whether the urine is obtained from healthy individuals or patients suffering from bladder cancer. PCR of β-actin only provides information regarding the sufficiency of genomic DNA. As such, β-actin PCR is independent of the DNA methylation status of genes. The design for β-actin primers is that they contain no CpG sites in the primer sequences (i.e., methylation independent).

For primer sets of β-actin, it is recommended that primer sets of the second round PCR should be designed prior to those of the first round PCR. Design of the second round PCR primer sets for β-actin is recommended using the following guidelines. First, the second round PCR β-actin primers must be bisulfite specific. The primers must hybridize to ≥4 cytosines that are not followed by guanine (i.e., non-CpG cytosines). Second, the second round PCR β-actin primers must amplify to yield an optimal length of amplicon. The resulting amplicon should allow adequate space for the first round β-actin primers to anneal. Preferably, the amplicon size is between ≥about 80 base pairs and ≤about 150 base pairs. Third, the second round PCR β-actin primers have a melting temperature (i.e., $T_M$) of ~60° C. Fourth, the second round PCR β-actin primers should avoid (i) a consecutive of >3 cytosines, or (ii) a consecutive of >3 cytosines and thymines in combination.

In accordance with the present invention, the second round PCR for β-actin is a real-time PCR. β-actin probes are designed using the following criteria: the probes must possess (i) the presence of non-CpG cytosine (e.g., ~4 cytosines); (ii) the absence of CpG dinucleotides; and (iii) a melting temperature of ~65° C. An exemplary TaqMan™ probe may be used and such probe is methylation independent but bisulfite specific.

Design of the first round PCR primer sets for β-actin is recommended using the following guidelines. First, the first round PCR β-actin primers must flank the second round PCR β-actin primers. Preferably, the first round PCR β-actin primers amplify an amplicon that is ~50 base pairs outside the second round PCR 5' end. Second, the amplicon size resulting from the first round PCR should be in the range of ≤350 base pairs. Third, the first round β-actin primers are DNA methylation independent (i.e., the primers contain no CpG sites in the primer sequence). Fourth, the first round PCR β-actin primers must be bisulfite specific (i.e., only amplify bisulfite treated DNA). The bisulfite specific β-actin primers preferably anneal to ≥4 non-CpG cytosines that are converted to uracil following bisulfite treatment. Use of bisulfite specific β-actin primers prevents a false positive PCR result. Fifth, the melting temperature of the first round PCR β-actin primers should be less than that of the second round PCR β-actin primers. In one embodiment, the melting temperature of the first round PCR β-actin primers is between ~45-55° C.; whereas the melting temperature of the second round PCR β-actin primers is ~60° C. This melting temperature requirement avoid potential annealing of the first round PCR β-actin primers during the second round PCR reaction—so as to avoid any potential interaction between the first and second round PCR primers, and thus prevents a false positive result. Sixth, the first round PCR β-actin primers should not anneal to ≥3 consecutive uracils or uracils/thymines.

Exemplary first round PCR β-actin primer set includes SEQ ID NO: 3 (forward primer) and SEQ ID NO: 4 (reverse primer). Exemplary second round PCR β-actin primer set includes SEQ ID NO: 12 (forward primer) and SEQ ID NO: 13 (reverse primer). Exemplary β-actin probe includes SEQ ID NO: 14.

The present methylation assay can detect methylation status of genes using less than 15 ml of urine from patients. The methylation status from the present assay correlates with the biopsy confirmation of bladder tumors. The present methylation assay has a high sensitivity and specificity. The present assay detects no methylation in healthy urine, as well as urine from prostate cancer, indicating specificity. The present methylation assay has a high positive predictive value, suggesting its usefulness in diagnosis and screening high-risk patients.

The present methylation assay detects the presence of higher grade and later stage cancers reliably. The present inventors observed a significant increase in BCL2 methylation in high grade bladder cancers. Contrary to the prior art, the present methylation assay detects about half of the low malignant and Ta bladder cancer patients. Our observation that five (5) of the seven (7) Ta stage tumors found negative by the present assay are also low malignancy potential grade (See, Table 1) suggests the methylation assay may be less sensitive for this tumor grade regardless of stage. Without wishing to be bound to a theory, it is speculated that low malignancy potential grade tumors release less cancer cells into the urine. Another alternative theory is that low malignancy potential grade tumor cells are more differentiated, and have less methylation at their CpG islands.

The present inventors observed no significant differences in methylation patterns seen between recurrent cancers and newly diagnosed cancers. Furthermore, the test did not detect any methylation in a patient who had no detectable tumors following a radical cystectomy, confirming the specificity of the assay. The patient had undergone surgery to remove a high grade tumor 5 weeks prior to the cystectomy. Urine analyzed was collected prior to the cystectomy and the final pathology on the removed organ showed no tumors. This suggests the methylation assay may have utility in monitoring patients after diagnosis and treatment for a recurrence.

It is another advantage of the present invention to use it in combination with other diagnostic methods and further provides a predictive value that may be specific and sensitive. Exemplary combination with two biomarkers is common. For example, Mansoor et at demonstrated that the combination of nuclear matrix protein (NMP-22), which has a sensitivity of about 45%, when combined with urine cytology had a 90% sensitivity and a 92% specificity, with a positive predictive value of 75% (Mansoor, Calam et al. 2008). Nisman, Yutkin et al reported that cytokeratin 19 fragment assay (CYFRA 21-1) has a sensitivity of 71.4% and a specificity of 68.6%, and therefore can yield false negative results that can lead to a high risk of progression of disease (Nisman, Yutkin et al. 2009). However, when they combined this assay with cytology and ultrasound, they reported a sensitivity of 90.5% (Nisman, Yutkin et al. 2009).

The present invention differs from many previously described prior art methylation assays. A distinct feature of the present invention is that it is a non-quantitative assay, whereas many prior art methylation assays are quantitative. In the quantitative methylation assay, they detect a quantitative amount of DNA methylation at the genes analyzed. In contrast, the present disclosed methylation assay provides qualitative results (i.e., "present" or "absence" of DNA methylation) of the genes analyzed.

The present invention unexpectedly provides an advantage in that it provides simple detection of DNA methylation. Many DNA methylation assays involve the use a single methylation specific PCR assay to detect DNA methylation. These methylation assays directly use extracted DNA as a template in its PCR reaction. As a result, these methylation assays suffer from insufficient sensitivity and requires greater PCR cycles.

The present invention further provides another unexpected advantage in that by utilizing a quantitative methylation specific PCR in the second round PCR, the present invention increases the specificity of the methyaltion assay. This increased specificity may be due to the fact that correct PCR amplification products need to be generated in both rounds of the PCRs. That is, the proper first round PCR ensures a resulting amplicon for the second round PCR to proceed. While the first round PCR is not a quantitative PCR, the second round PCR is a quantitative PCR that serves to quantify how much amplicons that contain the methylated DNA (i.e., due to methylation specific). Therefore, the second round PCR does not function to quantify the initial amount of the methylated DNA. The use of a TaqMan™ probe in the second round PCR also increases the specificity because this probe specifically hybridizes to a methylated DNA sequence. As a result, the present assay offers a higher specificity as compared to other conventional nested methylation specific PCR assays that utilize a conventional second round PCR and that visualize a PCR product by a gel based method.

The present invention also provides another unexpected advantage in that the first PCR amplification of the present invention provides initial DNA amplification during the plateau phase of the PCR. This results in generation of sufficient amplicon products (where DNA methylation is present in the sample) and permits the second PCR amplification for easy detection of methylation. In one embodiment, the second PCR amplification is characterized by the cycle number. Preferably, the amplification cycle number (i.e., $C_t$ value) is seen crossing the threshold value in a real time PCR.

The present invention further provides another unexpected advantage in that it has much less non-specific amplification. In methylation assays where a single methylation specific PCR is used, $C_t$ values are often greater than 30. (See, e.g., Friedrich et al. 2004). It is understood that it is common to detect non-specific amplification when the $C_t$ values are greater than 30. It is because there are primer-probe interactions during real time PCR. It is also understood that it is common to detect non-specific amplification even in control reactions (i.e., containing no template) when the PCR cycle is near 40. Therefore, methylation status data reported in prior art methylation assays (where a single methylation specific PCR is used) at Ct≥30 values are simply unreliable. Contrary to the prior art methylation assay, the present two-PCR methylation assay yields a much lower $C_t$ value (i.e., between 10 and 30), indicating elimination of the non-specific amplification.

In sum, the present invention provides a method of detecting bladder cancer in a human. The present method assesses the methylation status of CpG islands present on promoter of specific genes (e.g., BCL2, CDKNA and NID2). It is generally accepted that methylation of a gene relates to epigenetic silencing of the gene. It is also generally accepted that a higher degree of methylation is a manifestation of tumor progression. Without wishing to be bound by a theory, the present inventors discover a method of detecting bladder cancer, in particular low-grade bladder cancer, comprising detecting the methylation status of BCL2, CDKN2A, and NID2.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

Development of a Nested Methylation Specific PCR Assay

FIG. 1 depicts the general scheme of our nested methylation specific PCR assay. The assay involves a two-stage PCR: (i) first round PCR, and (ii) second round PCR (See, FIG. 1). After extraction of DNA from a collected biological sample, we treated the extracted DNA (~100-500 ng) with sodium bisulfite (~5M). The sodium bisulfite treatment enables the conversion of non-methylated cytosine to uracil in CpG islands, and thus permits the detection of methylation status when used with methylation specific PCR primers.

In this study, we selected a panel of genes to perform the nested methylation specific PCR; namely, the BCL2, CDKN2A, and NID2 genes. Three (3) respective forward primers (SEQ ID Nos. 1, 5 and 7) and three (3) respective reverse primers (SEQ ID Nos. 2, 6 and 8) were used in the first round PCR of amplification. β-actin (ACTB) serves as a control (i.e., forward primer—SEQ ID No. 3 and reverse primer—SEQ ID No. 4).

The three (3) pairs of PCR primers specifically amplify the region of DNA containing potential methylation sites within the BCL2, CDKN2A and NID2 genes. Note that the PCR amplification occurs independently of the methylation status of the genes because the primers hybridize to DNA lacking methylation sites. The first round PCR amplification occurs only towards the sodium bisulfite treated DNA, because the selected primers include several non-CpG cytosines (i.e., cytosines converted to uracils after the sodium bisulfite treatment), thus rendering them to be sodium bisulfite specific.

Next, we performed the second round PCR (after the generation of the corresponding amplicons from the first round PCR). The second round PCR is a nested methylation specific PCR reaction. To do so, we developed a real-time PCR assay to quantify the amount of gene methylation in BCL2, CDKN2A and NID2.

In these real-time PCR reactions, we prepared three (3) respective forward primers (i.e., SEQ ID Nos. 9, 15 and 19), three (3) respective reverse primers (i.e., SEQ ID Nos. 10, 16 and 19) and three (3) respective probes (i.e., SEQ ID. Nos. 11, 17 and 20) specific for BCL2, CDKN2A and NID2. The appearance of increasing fluorescence during the real-time PCR cycles indicates the presence of DNA methylation that is specific for the three respective targeted genes (i.e., BCL2, CDKN2A and NID2). In the second round PCR, β-actin was also used as a control (i.e., forward primer—SEQ ID No. 12, reverse primer—SEQ ID No. 13 and probe—SEQ ID No. 14).

Example 2

Nested Methylation Specific PCR Assay—Specifically Detects Methylated DNA for BCL2, CDKN2A, and NID2

Figure 2:
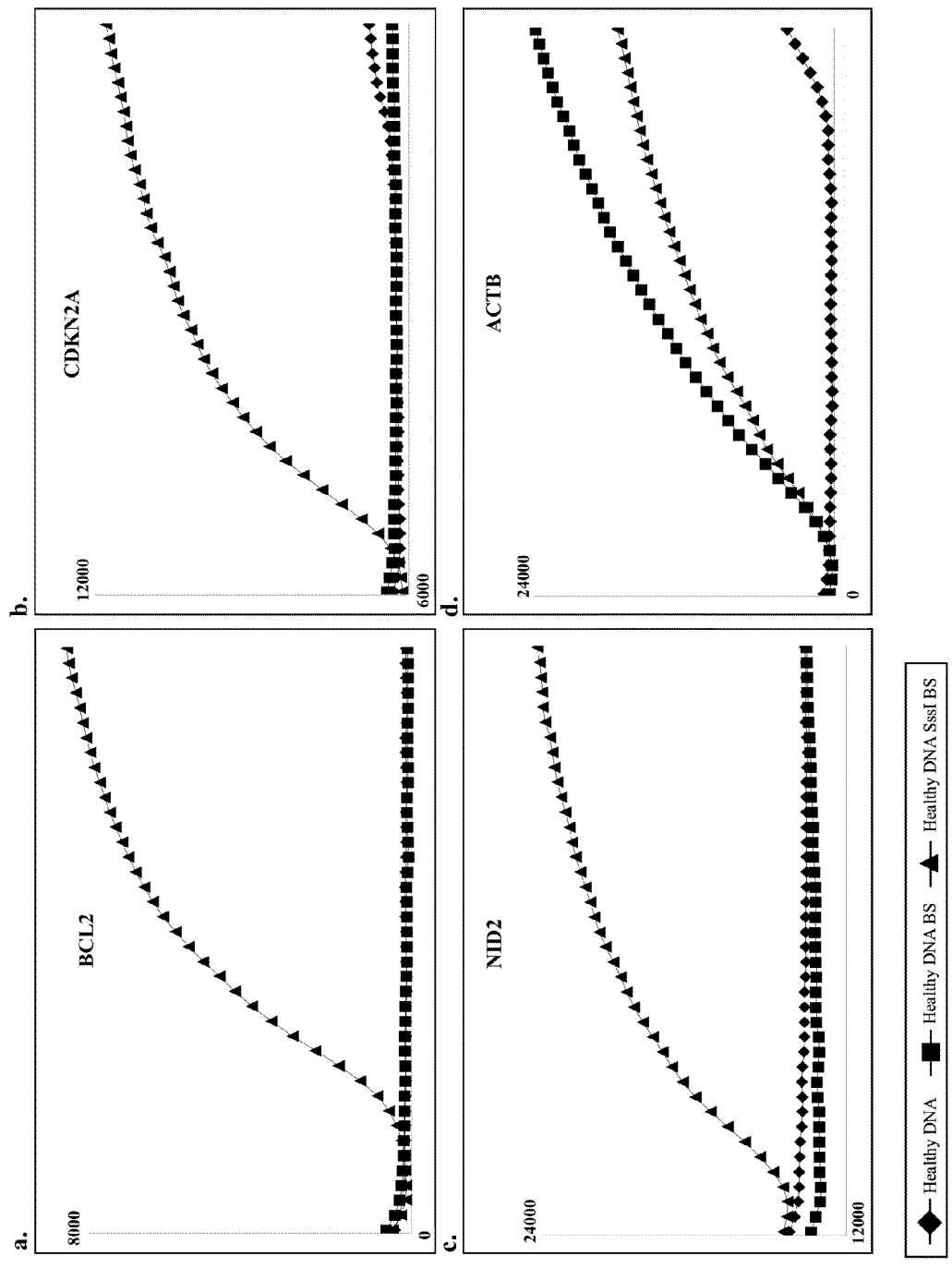
FIG. 2 depicts the specificity of DNA methylation and sodium bisulfite detection of the BCL2, CDKN2A, and NID2 nested methylation specific PCR assays.

FIG. 2 depicts a representative experiment showing that our nested methylation specific PCR assays for BCL2, CDKN2A, and NID2 genes are specific for methylated DNA. DNA amplification was not observed when unmethylated DNA was used or when DNA was not treated with sodium bisulfite. This indicates that DNA amplification is specific for methylated DNA templates.

In this study, template DNA used was total genomic DNA isolated from blood cells of healthy individuals. Sodium bisulfite treatment involves treating ~2 μg of isolated DNA with 5M sodium bisulfite for five (5) hours at approximately 60° C. Generation of hypermethylated DNA involves treating ~2 μg of isolated DNA with ~10 units of the bacterial CpG methyltransferase, SssI, in the presence of S-Adenosyl methionine.

We initially performed the first round PCR of the nested methylation specific PCR assay on three (3) DNA templates: (i) untreated genomic DNA from healthy patients (10 ng), (ii) genomic DNA that was sodium bisulfite treated (10 ng), and (iii) genomic DNA that was first hypermethylated and then sodium bisulfite treated (10 ng). To do so, we carried out four (4) separate PCR reactions: (i) BCL2, (ii) CDKN2A, (iii) NID2, and (iv) ACTB. With respect to the BCL2 gene we used forward (SEQ ID No. 1) and reverse (SEQ ID No. 2) primers. With respect to the CDKN2A gene we used forward (SEQ ID No. 5) and reverse (SEQ ID No. 6) primers. With respect to the NID2 gene we used forward (SEQ ID No. 7) and reverse (SEQ ID No. 8) primers. With respect to the ACTB gene we used forward (SEQ ID No. 3) and reverse (SEQ ID No. 4) primers.

We next performed the second round nested methylation specific PCR with a different set of second round primers and probes in reactions containing one tenth of the first round PCR reaction corresponding to the respective genes. With respect to the BCL2 gene we used forward primers (SEQ ID No. 9), reverse primers (SEQ ID No. 10), and fluorescently labeled probes (SEQ ID No. 11). With respect to the CDKN2A gene we used forward primers (SEQ ID No. 15), reverse primers (SEQ ID No. 16), and fluorescently labeled probes (SEQ ID No. 17). With respect to the NID2 gene we used forward primers (SEQ ID No. 18), reverse primers (SEQ ID No. 19), and fluorescently labeled probes (SEQ ID No. 20). With respect to the ACTB gene we used forward primers (SEQ ID No. 12), reverse primers (SEQ ID No. 13), and fluorescently labeled probes (SEQ ID No. 14).

The results of the first and second round nested methylation specific PCR for BCL2 is shown in FIG. 2 (panel a). The real-time amplification plots are the result of assaying each of the three (3) DNA templates with the first and second round primer sets for BCL2. Each point on the x-axis represents a single cycle out of forty (40) during PCR amplification and the y-axis represents the fluorescence reading after completion of each cycle. The plot marked by triangles represents amplification using the nested methylation specific PCR assay for BCL2 on genomic DNA that was both hypermethylated and sodium bisulfite treated. The templates denoted by diamonds and squares represent amplification using genomic DNA that was untreated and genomic DNA that was sodium bisulfite treated respectively. Note that the absence of any significant fluorescence before cycle thirty four (34) indicates that the region of the BCL2 gene that is potentially methylated was not amplified. Also note that the assay only produces amplification when the initial template is methylated at the BCL2 gene. Thus, the results show that the assay is specific for methylated DNA.

The results of the first and second round nested methylation specific PCR for CDKN2A is shown in FIG. 2 (panel b). Using a similar x and y axis representation, we observed a similar result for CDKN2A. The assay only produces amplification when the initial template is methylated at the CDKN2A gene.

The results of the first and second round nested methylation specific PCR for NID2 is shown in FIG. 2 (panel c). Using a similar x and y axis representation, we observed a similar result for NID2. The assay only produces amplification when the initial template is methylated at the NID2 gene.

The results of the first and second round nested methylation specific PCR for ACTB is shown in FIG. 2 (panel d). Using a similar x and y axis representation, we show that ACTB is a control for the presence of sufficient sodium bisulfite treated DNA. The assay only produces amplification when the initial template is sodium bisulfite treated. Also note that amplification occurs regardless of whether the template is methylated. Together, these results show that the ACTB gene is an excellent control for the presence of the sodium bisulfite converted DNA required for detection of DNA methylation.

Example 3

Clinical Studies—Using the Nested Methylation Specific PCR Assay

We utilized our developed nested methylation specific PCR assay to test the methylation pattern of selected genes in clinical studies. Patients who suffered from bladder cancer were recruited for the clinical studies. In this clinical study, we adapted our assay to use urine sediment as the DNA source, instead of DNA isolated from blood cells.

Human subjects without a diagnosis of bladder cancer were used as control. In total, urine samples from individuals were collected from control, as well as bladder cancer patients at Wolfson Medical Center (Israel). Urine samples were collected after diagnosis of bladder cancer but prior to surgical procedures. Physicians at the Wolfson Medical Center conducted diagnosis evaluation and performed surgery. The collected voided urine samples were immediately frozen at −80° C. prior to sending to the research facilities at Medical Diagnostic Laboratories (Hamilton, N.J.).

After thawing, the urine samples were divided into aliquots of ~15 ml. The urine sample aliquots were subjected to a brief centrifugation (i.e., 4,000 rcf, 5 minutes). DNA within the aliquots was extracted from the cell sediment present in the pellet after centrifugation of the sample. We digested the urine pellet (containing cells) with proteinase K (60 µg/mL) overnight, followed by phenol/chloroform (v/v=1:1) and ethanol precipitation. Extracted DNA (~500 ng) was treated with sodium bisulfite (5M). Approximately ten (10) nanograms of the extracted DNA were subjected to the nested methylation specific PCR assay for BCL2, CDKN2A, and NID2 genes, as well as ACTB control.

We analyzed the urine samples to examine the methylation status of the selected three (3) genes; namely BCL2, CDKN2A and NID2. ACTB was used as a control, and urine samples were included in the analysis if the DNA allowed robust amplification of the ACTB gene (i.e., amplification before cycle 25 in the real time PCR). The included samples were considered positive for cancer if one of the three (3) genes showed methylation based on the DNA amplification; as shown in example 2.

A total of 89 urine samples were tested and 64 were included based on the amplification seen for the control ACTB gene (See, Table 6). 42 of these samples were from bladder cancer patients and 22 were considered controls because they were not from bladder cancer patients. 34 out of the 42 urine samples from bladder cancer patients were methylation positive for one of the three (3) genes examined (i.e., 80.95% sensitivity). Specifically, only 26 patients were methylation positive for BCL2 (i.e., 61.9% sensitivity), only 3 patients were methylation positive for CDKN2A (i.e., 7.14% sensitivity), and only 26 patients were methylation positive for NID2 (i.e., 61.9% sensitivity). Finally, 3 out of 22 control patient samples were positive for DNA methylation (i.e., 86.36% specificity). In sum, 0% of completely healthy patients (i.e., no Urogenital disease diagnosed) were positive for DNA methylation at any of the three (3) genes and 81% of bladder cancer patients were positive at any of the three (3) genes when using DNA extracted from urine.

Example 4

DNA Methylation Status of BCL2, CDKN2A and NID2 Genes—Identifies Low Malignant Potential Bladder Cancer In this study, we correlate DNA methylation status of BCL2, CDKN2A and NID2 genes with low malignant potential bladder cancer. We used the nested methylation specific PCR assay to evaluate the DNA methylation status of these three (3) genes. Patients with low malignant potential bladder cancer have the best chance of survival, provided they are diagnosed early.

We collected a total of 11 patients who were diagnosed with bladder cancer with low malignant potential and that were included based on their DNA content. The 11 patients were included for the study because their urine DNA was positive for ACTB as described in example 3. We detected six (6) patients (out of 11 patients) that were positive for DNA methylation at one of the three (3) target genes (i.e., 54.54% sensitivity) (See, Table 1).

The first column denotes an assigned identification number. The second column denotes whether the patient whose sample was collected had a recurrence of their bladder cancer. The third column denotes the age of each patient if that data was available. The fourth column indicates each patients known age at the time of collection. Columns five (5), six (6), and seven (7) indicate whether or not the nested methylation specific PCR assay detected methylation at the indicated gene at the top of each column. Blank spaces indicate that no methylation was detected for that gene in that sample and a plus (+) sign indicates that methylation was detected. Columns eight (8), nine (9), and ten (10) show the type of cancer (i.e., TCC), the stage of cancer as determined by Wolfson Medical Center, and the grade of cancer.

In sum, out of the six (6) patients detected by the nested methylation specific PCR assay three (3) patients were detected by BCL2 methylation (i.e., 27.27% sensitivity), two (2) patients were exclusively detected by CDKN2A methylation (i.e., 18.18% sensitivity), and three (3) patients were detected by NID2 methylation (i.e., 27.27% sensitivity). The greatest sensitivity in detecting this stage of bladder cancer is achieved by detecting methylation with all three genes.

Example 5

DNA Methylation Status of BCL2, CDKN2A, and NID2 Genes—Identifies Low Grade Bladder Cancer In this study, we examined the methylation status of BCL2, CDKN2A, and NID2 genes and their association with low grade bladder cancers. We used the nested methylation specific PCR assay to evaluate the DNA methylation status of these three (3) genes. Low grade bladder cancer is more likely to recur as compared to low malignant potential bladder cancer.

We collected a total of 12 patients who were diagnosed with low grade bladder cancer and that were included based on their DNA content. The 12 patients were included for the study because their urine DNA was positive for ACTB as described in example 3. We detected ten (10) patients (out of 12 patients) that were positive for DNA methylation at one of the three (3) target genes (i.e., 83.33% sensitivity) (See, Table 2). Eight (8) patients detected positive for methylation of BCL2 (i.e., 66.67% sensitivity), no patients were positive for CDKN2A (i.e., 0% sensitivity), and eight (8) patients were positive for methylation of NID2 (i.e., 66.67% sensitivity).

Example 6

DNA Methylation Status of BCL2, CDKN2A and NID2 Genes—Identifies High Grade Bladder Cancer In this study, we evaluated the methylation status of BCL2, CDKN2A, and NID2 genes and their association with high grade bladder cancer. We used the nested methylation specific PCR assay to evaluate the DNA methylation status of these three (3) genes. High grade bladder cancer presents the most prominent cancer to recur and progress as compared to low grade and low malignant potential tumors.

We collected urine samples from 18 patients who had been diagnosed with high grade bladder cancer and that were included based on their DNA content. The 18 patients were included for the study because their urine DNA was positive for ACTB as described in example 3. We detected 17 patients (out of 18 patients) that were positive for DNA methylation at one of the three (3) target genes (i.e., 94.44% sensitivity) (See, Table 3). 15 patients were positive for methylation of BCL2 (i.e., 83.33% sensitivity), one (1) patient was positive for methylation of CDKN2A (i.e., 5.55% sensitivity), and fourteen patients were positive for methylation of NID2 (i.e., 77.77% sensitivity).

Example 7

DNA Methylation Status of BCL2, CDKN2A and NID2 Genes—Fails to Identify Other Cancers in Urine In this study, we evaluated the methylation status of BCL2, CDKN2A, and NID2 genes and their association with other non-bladder cancers. We used the nested methylation specific PCR assay to evaluate the DNA methylation status of these three (3) genes. These cancers are difficult to detect in urine because cancer cells from organs other than the bladder are not readily present in patient urine.

We collected urine samples from four (4) Renal Cancer patients (i.e., RCC), five (5) prostate cancer patients (i.e., CaP), one (1) neuroendocrine cancer patient, and one (1) breast cancer patient and they were included based on their DNA content. The 11 patients were included for the study because their urine DNA was positive for ACTB as described in example 3. We detected one (1) patient (out of 11 patients) that was positive for DNA methylation at one of the three (3) target genes (i.e., 9.09% sensitivity) (See, Table 4). No patients were positive for methylation of BCL2 (i.e., 0% sensitivity), no patients were positive for methylation of CDKN2A (i.e., 0% sensitivity), and one (1) patient was positive for methylation of NID2 (i.e., 9.09% sensitivity).

Example 8

DNA Methylation Status of BCL2, CDKN2A and NID2 Genes—Fails to Identify Healthy Patients in Urine In this study, we evaluated the methylation status of BCL2, CDKN2A, and NID2 genes and their association with healthy subjects and those with non-malignant Urogenital conditions. We used the nested methylation specific PCR assay to evaluate the DNA methylation status of these three (3) genes.

We collected urine samples, that were included based on their DNA content, from one (1) cured bladder cancer patient (i.e., no tumor after removal of bladder, cystectomy), two (2) patients with kidney stones, one (1) BPH patient (i.e., Benign prostatic hyperplasia), one (1) patient with inflammation, one (1) patient with cystitis, and five (5) patients who have not been diagnosed with any disease. The 11 patients were included for the study because their urine DNA was positive for ACTB as described in example 3. We detected two (2) patients (out of 11 patients) that were positive for DNA methylation at one of the three (3) target genes (i.e., 18.18% sensitivity) (See, Table 5). No patients were positive for methylation of BCL2 (i.e., 0% sensitivity), one patient was positive for methylation of CDKN2A (i.e., 9.09% sensitivity), and one (1) patient was positive for methylation of NID2 (i.e., 9.09% sensitivity).

Example 9

DNA Methylation Analysis of Genes Selected from Literature Cannot Distinguish Between Healthy and Cancer DNA In this study, we evaluated the methylation status of the BCL2, CDKN2A, NID2, TERT, EDNRB, RASSF1A, TNFRSF25, GSTP1, ARF, DAPK, and MGMT genes and their association with healthy subjects and those with bladder cancer. They were evaluated based on four (4) criteria: (i) whether the assays amplified DNA that was unmodified by sodium bisulfite, (ii) whether or not DNA methylation was detected in DNA extracted from healthy patients, (iii) whether the gene was able to be adapted to the nested methylation specific PCR assay to achieve the necessary sensitivity, and (iv) whether methylation at the gene had an additive effect to the overall sensitivity in detecting cancer using urine.

We synthesized real time PCR forward primers, reverse primers, and probes as reported in published articles on DNA methylation and bladder cancer. All of the assays were reported to be important in detecting bladder cancer in patient urine. In order to determine the first criteria required we evaluated the assays using DNA that was extracted from bladder cancer cell lines (T24) and that was not treated with sodium bisulfite. The DNA was used in single real time PCR reactions (10 ng) containing the forward primers, reverse primers, and probes. Results showed that the assay for EDNRB amplified DNA that was not treated with sodium bisulfite. This assay was excluded based on the possibility that using it would generate false positive results from DNA that was not fully converted by sodium bisulfite.

In order to determine the second criteria required we evaluated the assays using DNA extracted from the urine of healthy control subjects, a high grade bladder cancer patient, and DNA that was hypermethylated in vitro. The DNA (2 µg) was treated with sodium bisulfite (5 M) and used in single real time PCR reactions (10 ng) containing the forward primers, reverse primers, and probes. Results showed that the assays for RASSF1A and TNFRSF25 strongly detected DNA methylation in DNA extracted from a healthy patient who had no signs of bladder cancer. Furthermore, the assay for MGMT did not amplify DNA from any of templates. Note that this assay was reported to strongly amplify DNA using similar templates. These three (3) assays were excluded in that they had no value in distinguishing between healthy and cancer patients.

In order to achieve the required sensitivity in detecting DNA methylation in patient urine, as well as to determine the third criteria required, we generated first round sodium bisulfite specific primers for each gene that flanked the region amplified by the real time PCR primers. This was identical to the approach described in example 1. Several primers flanking the region of interest for each gene were tested as in example 2 using the same three (3) DNA templates: (i) untreated genomic DNA from healthy patients (10 ng), (ii) genomic DNA that was sodium bisulfite treated (10 ng), and (iii) genomic DNA that was first methylated and then sodium bisulfite treated (10 ng). Results of this experiment showed that a nested methylation specific PCR assay for the ARF gene could not be generated (i.e., the amplification generated with a two step PCR showed no improvement as compared to amplification seen when using a single real time methylation specific PCR). Note that the remaining genes that passed the first three criteria were BCL2, CDKN2A, NID2, TERT, GSTP1, and DAPK.

In order to determine the fourth criteria, DNA extracted from patient urine samples were assayed using the nested methylation specific PCR assays for BCL2, CDKN2A, NID2, TERT, GSTP1, and DAPK as in the clinical trial described in example 3. Results of this analysis determined that the highest sensitivity and specificity was obtained using BCL2, CDKN2A, and NID2. Though the other genes detected DNA methylation, the samples detected were also recognized by one of the former three genes (i.e., no additional samples were detected using these genes). Additionally, they detected a lower number of samples.

Experimental Methodology and Protocols a) Patients and Sample Collection

All study participants were provided with written informed consents, and the study protocol received approval from the Israeli Ministry of Health. Ministry of Health approval for the experimental protocol: 9-2008-0588, Genetic committee approval: 069-2008, Local IRB approval: 1019. Bladder cancer diagnosis was made by the attending physicians and confirmed by histological evaluation of the resected tissue samples. Clinical and pathological data for the population studied is shown in Table 1. Urine samples were collected at Wolfson Medical Center (Holon, Israel) either during outpatient visits or during the morning before the surgical procedure to treat the patient. Each sample was immediately frozen at −80° C. in 50 ml conical tubes and stored for a maximum of three months. The samples were then shipped on dry ice to our laboratories at Medical Diagnostic Laboratories, LLC (USA). Upon arrival the urine was thawed and aliquoted into 15 ml conical tubes and frozen at −80° C.

b) DNA Preparation and Sodium Bisulfite Treatment

Genomic DNA extracted from healthy patient samples was purchased from Promega (Madison, Wis.). Fully methylated DNA was generated by treating it with the SssI CpG methyltransferase (New England Biolabs, Ipswich, Mass.). For clinical samples, urine sediment was collected from 15 ml of urine by centrifugation at 4,000 RPM in a table top centrifuge. The pellet was washed with PBS and re-suspended in PBS containing 1% SDS and 120 µg/ml proteinase K. Samples were incubated at 42° C. over night. They were then extracted using phenol/chloroform followed by ethanol precipitation. DNA was re-suspended in 20 µl of distilled water, followed by sodium bisulfite treatment using the Epitect Bisulfite Kit (Qiagen, Valencia, Calif.) according to the manufacturer's directions. The detailed protocol is provided below:

1) Thaw frozen patient urine sample and place on ice.
2) Spin down 10 to 15 ml of urine in a 15 ml conical tube at 4,000 RPM for 5 minutes.
3) Aspirate the supernatant leaving about 500 µl of liquid at the bottom so as to not disturb the pellet.
4) Wash pellet with 10 ml PBS.
5) Centrifuge 5 min at 4,000 RPM.
6) Aspirate supernatant leaving about 500 µl PBS at the bottom of the tube.
7) Transfer pellet and PBS to a 1.7 ml eppendorf tube.
8) Add 50 µl of 10% SDS to make a final concentration of 1%.
9) Add 60 µg of proteinase K to the tube to make a final concentration of 120 µg/ml
10) Vortex tube and incubate at 42° C. over night.
11) Add 600 µl of phenol/chloroform to each tube and vortex.
12) Centrifuge 5 min at max speed in a microcentrifuge.
13) Remove aqueous phase and pipette into a clean 2 ml eppendorf tube.
14) Add 50 µl of 4M NaCl and 40 µg of molecular biology grade glycogen.
15) Add 1.5 ml of cold 100% ethanol and vortex tube.
16) Incubate in −80° C. freezer for 12 min.
17) Centrifuge tube 10 min at max speed in a microcentrifuge.
18) Remove supernatant without disturbing the pellet.
19) Add 1 ml of 70% ethanol to the pellet and vortex.
20) Centrifuge tube 5 min at max speed in a microcentrifuge.
21) Remove supernatant without disturbing the pellet.
22) Dry pellet 8 min in an Eppendorf Vacufuge plus Vacuum Concentrator.
23) Resuspend pellet in 20 µl of dH$_2$O (pellet may not completely resuspend).
24) Bisulfite treat DNA with the Qiagen Epitect Bisulfite kit.
25) Add 85 µl of the bisulfite mix to the partially resuspended pellet and add 35 µl of the DNA protect solution. Mix well by vortexing and do a quick spin to bring the contents to the bottom of the tube.
26) Add the entire solution including any of the pellet that did not resuspend into a PCR tube.
27) Run the program listed in the Epitect manual in a thermal cycler.
28) Remove the PCR tubes when cycling is finished and transfer to a 1.7 ml eppendorf tube. Transfer everything including any insoluable material.
29) Follow the clean up and desulfonation steps outlined in the manual. When adding the solution to the spin column make sure to transfer everything again. Elute using 25 µl of the provided elution buffer.

c) Nested Methylation Specific PCR

Each bisulfite treated DNA sample was amplified in four separate PCR reactions each containing 1 µl of extracted DNA, HotStart Taq polymerase, and the forward and reverse flanking primers for each gene tested. Thermal cycling for the first round PCR was 95° C. 30", 54-56° C. 1', 72° C. 1' for 40 cycles. The second round PCR was performed on a Mx3000 (Agilent Technologies, Santa Clara, Calif.) using 5 µl of the first round PCR, PerfeCTa™ qPCR SuperMix, Low ROX (Quanta BioBiosciences, Gaithersburg, Md.), and the corresponding real-time PCR primers and probe for each gene. The thermal cycling conditions were 15" at 95° C., 45" at 60-65° C. for 40 cycles. The details of the nested PCR is provided below:

1. For each bisulfite treated DNA set up a conventional first round PCR using the appropriate gene specific primers designed to flank methylated CpG islands. Genes tested are ACTB, BCL2, CDKN2A, and NID2 (i.e., 4 separate PCR's per DNA).

Mix:

| | |
|---|---|
| 10X Buffer | 5 μl |
| Hot Start Taq | 0.25 μl |
| 10 mM dNTP's | 1 μl |
| 10 μM fwd primer | 1 μl |
| 10 μM Rev primer | 1 μl |
| Bisulfite treated DNA | 1 μl |
| dH$_2$O | 40.75 μl |

2. Place tubes in thermal cycler and run the following program optimized for the tested genes and primer sets:

| | |
|---|---|
| 1. 95° C. | 5 min |
| 2. 95° C. | 30 sec |
| 3. 54° C.-56° C. | 1 min |
| 4. 72° C. | 1 min |
| 5. Go to step 2 | Loop 39X |
| 6. 72° C. | 5 min |
| 7. 4° C. | Hold | d) Detection of Methylation Using Real Time PCR

1. Using the nested PCR product as the template, set up Real Time PCR reactions using gene specific Taqman™ primer sets correlating to the same genes amplified in the first round nested PCR. Each reaction is performed in duplicate. (8 PCR's per original DNA).

Mix:

| | |
|---|---|
| 2X master mix | 10 μl |
| Template | 5 μl |
| 10 μM fwd primer | 1 μl |
| 10 μM Rev primer | 1 μl |
| 5 μM probe | 1 μl |
| dH2O | 2 μl |

2. Place plate in Real Time PCR machine and run the following program:

| | |
|---|---|
| 1. 95° C. | 5 min |
| 2. 95° C. | 15 sec |
| 3. 60° C.-65° C. | 45 sec (take reading at end of cycle) |
| 4. Go to step 2 | Loop 39X |

3. Analyze data to determine if any methylation at target genes is found. ACTB is used to determine DNA quality. Any amplification is recorded as positive methylation. Duplicate wells need to be consistent for a positive result.

e) Primer Sets

All primers and probes were purchased from IDT (Coralville, Iowa). Primers flanking the site of methylation used for first round PCR reactions were (5'-3'):

BCL2 fwd:
(SEQ ID NO: 1)
GAT GAA GTA TAT TTA TTA TAA GTT GT,

BCL2 rev:
(SEQ ID NO: 2)
CAA ATA AAC CAC AAA TAA CAC,

ACTB fwd:
(SEQ ID NO: 3)
GAT ATA AGG TTA GGG ATA GGA T,

ACTB rev:
(SEQ ID NO: 4)
AAA AAC TAC TTA TTC AAT TCA C,

CDKN2A fwd:
(SEQ ID NO: 5)
TTG GTT GGT TAT TAG AGG GT,

CDKN2A rev:
(SEQ ID NO: 6)
CTA AAA ACT CCC CAA AAA ACC T,

NID2 fwd:
(SEQ ID NO: 7)
GTT TAT TTG TTT TTA GGT GGT TAG,

NID2 rev:
(SEQ ID NO: 8)
CTC TCC CAA ATA AAC ACC AAC.

Primers and probes for detection of methylated cytosine in the second round PCR were:

BCL2 fwd:
(SEQ ID NO: 9)
TCG TAT TTC GGG ATT CGG TC,

BCL2 rev:
(SEQ ID NO: 10)
AAC TAA ACG CAA ACC CCG C,

BCL2 probe:
(SEQ ID NO: 11)
6FAM 5' ACG ACG CCG AAA ACA ACC GAA ATC TAC A BHQ1,

ACTB fwd:
(SEQ ID NO: 12)
TGG TGA TGG AGG AGG TTT AGT AAG T,

ACTB rev:
(SEQ ID NO: 13)
AAC CAA TAA AAC CTA CTC CTC CCT TAA,

ACTB probe:
(SEQ ID NO: 14)
6FAM 5' ACC ACC ACC CAA CAC ACA ATA ACA AAC ACA BHQ1, CDKN2A fwd:
(SEQ ID NO: 15)
TTA TTA GAG GGT GGG GCG GAT CGC, CDKN2A rev:
(SEQ ID NO: 16)
GAC CCC GAA CCG CGA CCG TAA, CDKN2A probe:
(SEQ ID NO: 17)
6FAM 5' AGT AGT ATG GAG TCG GCG GCG GG BHQ1, NID2 fwd:
(SEQ ID NO: 18)
TCG GTA TAG GAT TCG GTT TTT GTC G, NID2 rev:
(SEQ ID NO: 19)
CAC TCA AAA CTT CCC CAA AAA AAC GC, NID2 probe:
(SEQ ID NO: 20)
6FAM 5' CGA TGG TCG GGA AGT CGG TGG GGA AAT T BHQ1.

f) Analysis of Methylation Results

ACTB amplification was utilized to determine if a sample was valid based on DNA quality. An ACTB Ct score greater than 25 in the nested PCR was considered invalid. For methylated gene targets any amplification less than Ct=30 was considered positive. If any marker was positive for methylation, then the sample was considered positive for cancer.

g) Statistical Analysis

To obtain two-sided P value, sensitivity, specificity, and predictive powers, Fisher's exact test was performed using GraphPad InStat version 3.06 for Windows (GraphPad Software, San Diego Calif. USA).

All publications and patents cited in this specification are herein incorporated by reference in their entirety. Although the invention has been described in connection with specific preferred embodiments and certain working examples, it should be understood that the invention as claimed should not be unduly limited to such specific embodiments. Various modifications and variations of the described composition, method, and systems of the invention will be apparent to those skilled in the art without departing from the scope and spirit of the invention.

REFERENCES

Brait M, Begum S, et al. (2008). Aberrant promoter methylation of multiple genes during pathogenesis of bladder cancer. Cancer Epidemiol Biomarkers Prev 17(10): 2786-94.

Chung W, Bondaruk J, et al. (2011). Detection of bladder cancer using novel DNA methylation biomarkers in urine sediments. Cancer Epidemiol Biomarkers Prev 20(7): 1483-91.

Costa V L, Henrique R, et al. (2010). Three epigenetic biomarkers, GDF15, TMEFF2, and VIM, accurately predict bladder cancer from DNA-based analyses of urine samples. Clin Cancer Res 16(23): 5842-51.

Dulaimi E, Uzzo R G, et al. (2004). Detection of bladder cancer in urine by a tumor suppressor gene hypermethylation panel. Clin Cancer Res 10(6): 1887-93.

Friedrich M G, Weisenberger D J, et al. (2004). Detection of methylated apoptosis-associated genes in urine sediments of bladder cancer patients. Clin Cancer Res 10(22): 7457-65.

Hogue M O, Begum S, et al. (2006). Quantitation of promoter methylation of multiple genes in urine DNA and bladder cancer detection. J Natl Cancer Inst 98(14): 996-1004.

Hogue M O, Kim M S, et al. (2008). Genome-wide promoter analysis uncovers portions of the cancer methylome. Cancer Res 68(8): 2661-70.

Reinert T, Modin C, et al. (2011). Comprehensive genome methylation analysis in bladder cancer: identification and validation of novel methylated genes and application of these as urinary tumor markers. Clin Cancer Res 17(17): 5582-92.

Renard I, Joniau S, et al. (2009). Identification and validation of the methylated TWIST1 and NID2 genes through real-time methylation-specific polymerase chain reaction assays for the noninvasive detection of primary bladder cancer in urine samples. Eur Urol 58(1): 96-104.

Siegel R, Ward E, et al. (2011). Cancer statistics, 2011: the impact of eliminating socioeconomic and racial disparities on premature cancer deaths. CA Cancer J Clin 61(4): 212-36.

Valenzuela M T, Galisteo R, et al. (2002). Assessing the use of p16(INK4a) promoter gene methylation in serum for detection of bladder cancer. Eur Urol 42(6): 622-8; discussion 628-30.

Vinci S, Giannarini G, et al. (2009). Quantitative methylation analysis of BCL2, hTERT, and DAPK promoters in urine sediment for the detection of non-muscle-invasive urothelial carcinoma of the bladder: a prospective, two-center validation study. Urol Oncol 29(2): 150-6.

TABLE 1

| Patient | Recurrence | Age | Sex | BCL2 | CDKN2A | NID2 | Cancer | Stage | Grade |
|---|---|---|---|---|---|---|---|---|---|
| 31 | yes | 74 | M | + | | + | TCC | pTa | Low Malignant Potential |
| 32 | yes | 67 | M | | | + | TCC | pTa | Low Malignant Potential |
| 33 | no | 61 | F | | + | | TCC | pTa | Low Malignant Potential |
| 34 | no | 56 | n/a | | | | TCC | pTa | Low Malignant Potential |
| 35 | no | 62 | M | | | | TCC | pTa | Low Malignant Potential |
| 36 | no | 87 | M | + | | + | TCC | pTa | Low Malignant Potential |
| 37 | no | 86 | F | | + | | TCC | pTa | Low Malignant Potential |
| 38 | n/a | 87 | M | | | | TCC | pTa | Low Malignant Potential |
| 39 | n/a | n/a | n/a | | | | TCC | pTa | Low Malignant Potential |
| 40 | n/a | n/a | F | + | | | TCC | pTa | Low Malignant Potential |
| 41 | n/a | n/a | n/a | | | | TCC | pTa | Low Malignant Potential | n/a: not available
TCC: transitional cell carcinoma of the bladder

TABLE 2

| Patient | Recurrence | Age | Sex | BCL2 | CDKN2A | NID2 | Cancer | Stage | Grade |
|---|---|---|---|---|---|---|---|---|---|
| 19 | yes | 76 | M | + | | + | TCC | pT1 | Low grade |
| 20 | yes | 83 | M | + | | + | TCC | pT1 | Low grade |
| 21 | yes | 84 | M | | | + | TCC | pT1 | Low grade |
| 22 | no | 72 | M | + | | + | TCC | pT1 | Low grade |
| 23 | yes | 82 | F | | | | TCC | pTa | Low grade |
| 24 | yes | 82 | M | + | | + | TCC | pTa | Low grade |
| 25 | no | 77 | M | + | | + | TCC | pTa | Low grade |
| 26 | no | 56 | M | | | | TCC | pTa | Low grade |

TABLE 2-continued

| Patient | Recurrence | Age | Sex | BCL2 | CDKN2A | NID2 | Cancer | Stage | Grade |
|---|---|---|---|---|---|---|---|---|---|
| 27 | no | 80 | M | | | + | TCC | pTa | Low grade |
| 28 | no | n/a | M | + | | + | TCC | pTa | Low grade |
| 29 | yes | 78 | F | + | | | TCC | pTa | Low grade |
| 30 | yes | 78 | M | + | | | TCC | unknown | Low grade | n/a: not available
TCC: transitional cell carcinoma of the bladder

TABLE 3

| Patient | Recurrence | Age | Sex | BCL2 | CDKN2A | NID2 | Cancer | Stage | Grade |
|---|---|---|---|---|---|---|---|---|---|
| 1 | n/a | n/a | n/a | + | | + | TCC | pT3 | High grade |
| 2 | yes | 74 | M | + | | + | TCC | pT2 | High grade |
| 3 | yes | 85 | M | + | | + | TCC | pT2 | High grade |
| 4 | no | 77 | M | + | | + | TCC | pT2 | High grade |
| 5 | no | 68 | M | + | | + | TCC | pT2 | High grade |
| 6 | no | 77 | M | + | | + | TCC | pT2 | High grade |
| 7 | n/a | n/a | n/a | + | | + | TCC | pT2 | High grade |
| 8 | n/a | n/a | n/a | + | | + | TCC | pT2 | High grade |
| 9 | n/a | 56 | M | + | | | TCC | pT2 | High grade |
| 10 | yes | 64 | M | | | + | TCC | pT1 | High grade |
| 11 | yes | 76 | M | | | + | TCC | pT1 | High grade |
| 12 | no | 55 | M | | | | TCC | pT1 | High grade |
| 13 | no | 83 | M | + | | + | TCC | pT1 | High grade |
| 14 | no | 83 | M | + | | | TCC | pT1 | High grade |
| 15 | no | 79 | M | + | | + | TCC | pT1 | High grade |
| 16 | n/a | 73 | F | + | + | + | TCC | pT1 | High grade |
| 17 | n/a | n/a | n/a | + | | + | TCC | pT1 | High grade |
| 18 | yes | 77 | M | + | | | TCC | pT1 | High grade | n/a: not available
TCC: transitional cell carcinoma of the bladder

TABLE 4

| Patient | Recurrence | Age | Sex | BCL2 | CDKN2A | NID2 | Cancer | Stage | Grade |
|---|---|---|---|---|---|---|---|---|---|
| 44 | n/a | 52 | M | | | | RCC | NA | NA |
| 45 | n/a | 54 | M | | | | RCC | NA | NA |
| 46 | no | 45 | F | | | + | RCC | NA | NA |
| 47 | no | 75 | F | | | | RCC | NA | NA |
| 48 | n/a | 59 | M | | | | CaP | NA | NA |
| 49 | n/a | 71 | M | | | | CaP | NA | NA |
| 50 | n/a | 63 | M | | | | CaP | NA | NA |
| 51 | n/a | 66 | M | | | | CaP | NA | NA |
| 52 | n/a | 71 | M | | | | CaP | NA | NA |
| 53 | no | 76 | F | | | | Breast cancer | NA | NA |
| 54 | no | 75 | M | | | | neuroendocrine carcinoma | NA | NA | n/a: not available
RCC: Renal cancer
CaP: Prostate cancer
NA: not applicable

TABLE 5

| Patient | Recurrence | Age | Sex | BCL2 | CDKN2A | NID2 | Cancer | Stage | Grade |
|---|---|---|---|---|---|---|---|---|---|
| 55 | n/a | 74 | M | | | | Cystitis | NA | NA |
| 56 | n/a | 57 | M | | + | | kidney stones | NA | NA |
| 57 | n/a | 43 | M | | | | kidney stones | NA | NA |
| 58 | n/a | 81 | M | | | + | BPH | NA | NA |
| 59 | no | 60 | M | | | | inflammation | NA | NA |
| 60 | n/a | 40 | F | | | | healthy | NA | NA |
| 61 | n/a | 47 | F | | | | healthy | NA | NA |
| 62 | n/a | 55 | F | | | | healthy | NA | NA |
| 63 | n/a | 36 | M | | | | healthy | NA | NA |
| 64 | n/a | 43 | M | | | | healthy | NA | NA | n/a: not available
BPH: Enlarged Prostate
NA: not applicable

TABLE 6

|  | Any Gene | BCL2 | CDKN2A | NID2 | ACTB |  |
|---|---|---|---|---|---|---|
| Bladder Cancer/TCC | 34/42 | 26/42 | 3/42 | 26/42 | 42/52 | TCC |
| Low malignant Potential | 6/11 | 3/11 | 2/11 | 3/11 | | |
| Low grade | 10/12 | 8/12 | 0/12 | 8/12 | | |
| High Grade | 17/18 | 15/18 | 1/18 | 14/18 | | |
| pTa | 11/18 | 7/18 | 2/18 | 7/18 | | |
| pT1 | 12/13 | 9/13 | 1/13 | 10/13 | | |
| pT2/pT3 | 9/9 | 9/9 | 0/9 | 8/9 | | |
| unknown TCC | 1/1 | 0/1 | 0/1 | 1/1 | | |
| Controls | 3/22 | 0/22 | 1/22 | 2/22 | | Controls |
| Cystectomy, no tumor | 0/1 | 0/1 | 0/1 | 0/1 | 1/1 | |
| Renal Cancer | 1/4 | 0/4 | 0/4 | 1/4 | 4/11 | |
| Prostate Cancer | 0/5 | 0/5 | 0/5 | 0/5 | 5/9 | |
| Kidney Stones | 1/2 | 0/2 | 1/2 | 0/2 | 2/2 | |
| BPH | 1/1 | 0/1 | 0/1 | 1/1 | 1/1 | |
| Neuroendocrine Cancer | 0/1 | 0/1 | 0/1 | 0/1 | 1/1 | |
| Breast Cancer | 0/1 | 0/1 | 0/1 | 0/1 | 1/1 | |
| Inflammation | 0/1 | 0/1 | 0/1 | 0/1 | 1/1 | |
| Healthy | 0/5 | 0/5 | 0/5 | 0/5 | 5/9 | |
| Cystitis | 0/1 | 0/1 | 0/1 | 0/1 | 1/1 | |
| Total | | | | | 64/89 | |
| sensitivity | 0.8095 | 0.6190 | 0.0714 | 0.6190 | 0.7190 | |
| specificity | 0.8636 | 1.000 | 0.9545 | 0.9091 | | |
| Positive Predictive Value | 0.9189 | 1.000 | 0.7500 | 0.9286 | | |
| Negative Predictive Value | 0.7037 | 0.5789 | 0.3500 | 0.5556 | | |
| P value | <0.0001 | <0.0001 | 1.000 | <0.0001 | | |

TABLE 7

First Round PCR Primers

| Primer Name | Primer Sequence | SEQ ID NO. |
|---|---|---|
| BCL2 fwd | GAT GAA GTA TAT TTA TTA TAA GTT GT | SEQ ID NO. 1 |
| BCL2 rev | CAA ATA AAC CAC AAA TAA CAC | SEQ ID NO. 2 |
| ACTB fwd | GAT ATA AGG TTA GGG ATA GGA T | SEQ ID NO. 3 |
| ACTB rev | AAA AAC TAC TTA TTC AAT TCA C | SEQ ID NO. 4 |
| CDKN2A fwd | TTG GTT GGT TAT TAG AGG GT | SEQ ID NO. 5 |
| CDKN2A rev | CTA AAA ACT CCC AAA AAC ACC T | SEQ ID NO. 6 |
| NID2 fwd | GTT TAT TTG TTT TTA GGT GGT TAG | SEQ ID NO. 7 |
| NID2 rev | CTC TCC AAA ATA AAC ACC AAC | SEQ ID NO. 8 |

TABLE 8

Second Round Real Time PCR Primers

| Primer Name | Primer Sequence | SEQ ID NO. |
|---|---|---|
| BCL2 fwd | TCG TAT TTC GGG ATT CGG TC | SEQ ID NO. 9 |
| BCL2 rev | AAC TAA ACG CAA ACC CCG C | SEQ ID NO. 10 |
| BCL2 probe | ACG ACG CCG AAA ACA ACC GAA ATC TAC A | SEQ ID NO. 11 |
| ACTB fwd | TGG TGA TGG AGG AGG TTT AGT AAG T | SEQ ID NO. 12 |
| ACTB rev | AAC CAA TAA AAC CTA CTC CTC CCT TAA | SEQ ID NO. 13 |
| ACTB probe | ACC ACC ACC CAA CAC ACA ATA ACA AAC ACA | SEQ ID NO. 14 |
| CDKN2A fwd | TTA TTA GAG GGT GGG GCG GAT CGC | SEQ ID NO. 15 |
| CDKN2A rev | GAC CCC GAA CCG CGA CCG TAA | SEQ ID NO. 16 |
| CDKN2A probe | AGT AGT ATG GAG TCG GCG GCG GG | SEQ ID NO. 17 |

TABLE 8-continued

Second Round Real Time PCR Primers

| Primer Name | Primer Sequence | SEQ ID NO. |
|---|---|---|
| NID2 fwd | TCG GTA TAG GAT TCG GTT TTT GTC G | SEQ ID NO. 18 |
| NID2 rev | CAC TCA AAA CTT CCC CAA AAA AAC GC | SEQ ID NO. 19 |
| NID2 probe | CGA TGG TCG GGA AGT CGG TGG GAA T | SEQ ID NO. 20 |

What is claimed is:

1. A method of determining an increased risk of bladder cancer in a human, comprising the steps of:
   (a) obtaining a urine sample from a human;
   (b) isolating genomic DNA from said urine;
   (c) exposing said isolated genomic DNA with sodium bisulfite;
   (d) performing a first round PCR on said sodium bisulfite-treated genomic DNA to amplify a methylation site present on a CpG island, said CpG island is present on a plurality of genes consisting of BCL2, CDKN2A, and NID2,
      said first round PCR is performed using a forward primer and a reverse primer for BCL2, CDKN2A, and NID2 respectively, said forward primers consisting of the nucleotide sequence of SEQ ID NO: 1 (for BCL2), SEQ ID NO: 5 (for CDKN2A), and SEQ ID NO: 7 (for NID2) and said reverse primers consisting of the nucleotide sequence of SEQ ID NO: 2 (for BCL2), SEQ ID NO: 6 (for CDKN2A), and SEQ ID NO: 8 (for NID2);
   (e) performing a second round PCR to detect DNA methylation status on said methylation site, said second round PCR is a methylation-specific PCR; and
   (f) determining an increased risk of bladder cancer in said human,
   wherein the detection of DNA methylation status on said CpG island of said plurality of genes in said urine sample is indicative of an increased risk of bladder cancer in said human.

2. The method of claim 1, after step (c), further comprising the step of: (c') performing a real time PCR to amplify β-actin on said sodium bisulfite-treated genomic DNA, wherein a Ct value of ≤25 is indicative of a sufficient amount of sodium bisulfite treated genomic DNA in said urine.

3. The method of claim 1, wherein said second round PCR is performed using a forward primer and a reverse primer for BCL2, CDKN2A, and NID2 respectively, said forward primers consisting of the nucleotide sequence of SEQ ID NO: 9 (for BCL2), SEQ ID NO: 15 (for CDKN2A), and SEQ ID NO: 18 (for NID2) and said reverse primers consisting of the nucleotide sequence of SEQ ID NO: 10 (for BCL2), SEQ ID NO: 16 (for CDKN2A), and SEQ ID NO: 19 (for NID2).

4. The method of claim 1, wherein said second round PCR is performing using a probe for BCL2, CDKN2A, and NID2 respectively, said probe consisting of the nucleotide sequence of SEQ ID NO: 11 (for BCL2), SEQ ID NO: 17 (for CDKN2A) and SEQ ID NO: 20 (for NID2).

5. The method of claim 2, wherein said first round PCR is performed using a forward primer and a reverse primer for β-actin, said forward primer consisting of the nucleotide sequence of SEQ ID NO: 3, and said reverse primer consisting of the nucleotide sequence of SEQ ID NO: 4 (for BCL2).

6. The method of claim 2, wherein said second round PCR is performed using a forward primer and a reverse primer for β-actin, said forward primer consisting of the nucleotide sequence of SEQ ID NO: 12, and said reverse primer having a nucleotide sequence of SEQ ID NO: 13.

7. The method of claim 2, wherein said second round PCR is performing using a probe for β-actin, said probe consisting of the nucleotide sequence of SEQ ID NO: 14.

8. The method of claim 1, wherein said bladder cancer is a low malignant potential bladder cancer.

9. The method of claim 8, wherein said low malignant potential bladder cancer is transitional cell carcinoma.

* * * * *

SEQUENCE LISTING

<160> NUMBER OF SEQ ID NOS: 20

<210> SEQ ID NO 1
<211> LENGTH: 26
<212> TYPE: DNA
<213> ORGANISM: Homo sapiens

<400> SEQUENCE: 1
gatgaagtat atttattata agttgt                                           26

<210> SEQ ID NO 2
<211> LENGTH: 21
<212> TYPE: DNA
<213> ORGANISM: Homo sapiens

<400> SEQUENCE: 2
caaataaacc acaaataaca c                                                21

<210> SEQ ID NO 3
<211> LENGTH: 22
<212> TYPE: DNA
<213> ORGANISM: Homo sapiens

<400> SEQUENCE: 3
gatataaggt tagggatagg at                                               22

<210> SEQ ID NO 4
<211> LENGTH: 22
<212> TYPE: DNA
<213> ORGANISM: Homo sapiens

<400> SEQUENCE: 4
aaaaactact tattcaattc ac                                               22

<210> SEQ ID NO 5
<211> LENGTH: 20
<212> TYPE: DNA
<213> ORGANISM: Homo sapiens

<400> SEQUENCE: 5
ttggttggtt attagagggt                                                  20

<210> SEQ ID NO 6
<211> LENGTH: 22
<212> TYPE: DNA
<213> ORGANISM: Homo sapiens

<400> SEQUENCE: 6
ctaaaaactc cccaaaaaac ct                                               22

<210> SEQ ID NO 7

```
<211> LENGTH: 24
<212> TYPE: DNA
<213> ORGANISM: Homo sapiens

<400> SEQUENCE: 7
gtttatttgt ttttaggtgg ttag                                      24

<210> SEQ ID NO 8
<211> LENGTH: 21
<212> TYPE: DNA
<213> ORGANISM: Homo sapiens

<400> SEQUENCE: 8
ctctcccaaa taaacaccaa c                                         21

<210> SEQ ID NO 9
<211> LENGTH: 20
<212> TYPE: DNA
<213> ORGANISM: Homo sapiens

<400> SEQUENCE: 9
tcgtatttcg ggattcggtc                                           20

<210> SEQ ID NO 10
<211> LENGTH: 19
<212> TYPE: DNA
<213> ORGANISM: Homo sapiens

<400> SEQUENCE: 10
aactaaacgc aaaccccgc                                            19

<210> SEQ ID NO 11
<211> LENGTH: 28
<212> TYPE: DNA
<213> ORGANISM: Homo sapiens

<400> SEQUENCE: 11
acgacgccga aaacaaccga aatctaca                                  28

<210> SEQ ID NO 12
<211> LENGTH: 25
<212> TYPE: DNA
<213> ORGANISM: Homo sapiens

<400> SEQUENCE: 12
tggtgatgga ggaggtttag taagt                                     25

<210> SEQ ID NO 13
<211> LENGTH: 27
<212> TYPE: DNA
<213> ORGANISM: Homo sapiens

<400> SEQUENCE: 13
aaccaataaa acctactcct cccttaa                                   27

<210> SEQ ID NO 14
<211> LENGTH: 30
<212> TYPE: DNA
<213> ORGANISM: Homo sapiens

<400> SEQUENCE: 14
accaccaccc aacacacaat aacaaacaca                                30
```

```
<210> SEQ ID NO 15
<211> LENGTH: 24
<212> TYPE: DNA
<213> ORGANISM: Homo sapiens

<400> SEQUENCE: 15
ttattagagg gtggggcgga tcgc                                          24

<210> SEQ ID NO 16
<211> LENGTH: 21
<212> TYPE: DNA
<213> ORGANISM: Homo sapiens

<400> SEQUENCE: 16
gaccccgaac cgcgaccgta a                                             21

<210> SEQ ID NO 17
<211> LENGTH: 23
<212> TYPE: DNA
<213> ORGANISM: Homo sapiens

<400> SEQUENCE: 17
agtagtatgg agtcggcggc ggg                                           23

<210> SEQ ID NO 18
<211> LENGTH: 25
<212> TYPE: DNA
<213> ORGANISM: Homo sapiens

<400> SEQUENCE: 18
tcggtatagg attcggtttt tgtcg                                         25

<210> SEQ ID NO 19
<211> LENGTH: 26
<212> TYPE: DNA
<213> ORGANISM: Homo sapiens

<400> SEQUENCE: 19
cactcaaaac ttccccaaaa aaacgc                                        26

<210> SEQ ID NO 20
<211> LENGTH: 28
<212> TYPE: DNA
<213> ORGANISM: Homo sapiens

<400> SEQUENCE: 20
cgatggtcgg gaagtcggtg gggaaatt                                      28
```